US009657352B2

(12) United States Patent
Getman

(10) Patent No.: US 9,657,352 B2
(45) Date of Patent: May 23, 2017

(54) COMPOSITIONS AND METHODS FOR DETECTING BV-ASSOCIATED BACTERIAL NUCLEIC ACID

(75) Inventor: Damon Kittredge Getman, Poway, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 57 days.

(21) Appl. No.: 14/113,880

(22) PCT Filed: Apr. 25, 2012

(86) PCT No.: PCT/US2012/035019
§ 371 (c)(1),
(2), (4) Date: Oct. 25, 2013

(87) PCT Pub. No.: WO2012/149034
PCT Pub. Date: Nov. 1, 2012

(65) Prior Publication Data
US 2014/0065617 A1    Mar. 6, 2014

Related U.S. Application Data

(60) Provisional application No. 61/478,753, filed on Apr. 25, 2011.

(51) Int. Cl.
*C12Q 1/68*    (2006.01)
(52) U.S. Cl.
CPC .................... *C12Q 1/689* (2013.01)
(58) Field of Classification Search
CPC ..................................................... C12Q 1/689
See application file for complete search history.

(56) References Cited

U.S. PATENT DOCUMENTS

| 6,110,678 A | * | 8/2000 | Weisburg et al. | ............ | 435/6.12 |
| 2011/0212852 A1 | * | 9/2011 | Getman | ............................ | 506/9 |
| 2012/0264126 A1 | * | 10/2012 | Johnson et al. | ............. | 435/6.11 |

FOREIGN PATENT DOCUMENTS

| EP | 1 726 662 A1 | | 11/2006 | | |
| WO | WO9622392 | * | 7/1996 | ............... | C12Q 1/68 |
| WO | WO2011068679 | * | 9/2011 | ............... | C12Q 1/68 |

OTHER PUBLICATIONS

Mothershed EA, Whitney AM. Nucleic acid-based methods for the detection of bacterial pathogens: present and future considerations for the clinical laboratory. Clin Chim Acta. Jan. 2006; 363(1-2):206-20. Epub Sep. 1, 2005. Review.*
Genbank Accession No. AF283705- Megasphaera elsdenii strain La03 16S ribosomal RNA gene, partial sequence (GI: 9971952, submitted by Ouwerkerk et al. Jun. 30, 2000, retrieved on Mar. 15, 2015 from http://www.ncbi.nlm.nih.gov/nuccore/AF283705).*
Lowe T, Sharefkin J, Yang SQ, Dieffenbach CW. A computer program for selection of oligonucleotide primers for polymerase chain reactions. Nucleic Acids Res.Apr. 11, 1990; 18(7):1757-61.*
Ferris MJ, Masztal A, Martin DH. Use of species-directed 16S rRNA gene PCR primers for detection of Atopobium vaginae in patients with bacterial vaginosis. J Clin Microbiol. Dec. 2004;42(12):5892-4.*
Kutyavin IV, Afonina IA, Mills A, Gorn VV, Lukhtanov EA, Belousov ES, Singer MJ, Walburger DK, Lokhov SG, Gall AA, Dempcy R, Reed MW, Meyer RB, Hedgpeth J. 3'-minor groove binder-DNA probes increase sequence specificity at PCR extension temperatures. Nucleic Acids Res. Jan. 15, 2000; 28(2):655-61.*
Marras SA. Interactive fluorophore and quencher pairs for labeling fluorescent nucleic acid hybridization probes. Mol Biotechnol. Mar. 2008; 38(3):247-55. Epub Nov. 6, 2007.*
Thelwell N, Millington S, Solinas A, Booth J, Brown T. Mode of action and application of Scorpion primers to mutation detection. Nucleic Acids Res. Oct. 1, 2000; 28(19):3752-61.*
EPO Communication, European Patent Application No. 12717575.0-1406, dated Dec. 22, 2014.
Doyle LM, et al., "Sequence of the gene encoding the 16S rRNA of the beer spoilage organism Megasphaera cerevisiae," J Ind Microbiol. Aug. 1995, pp. 67-70, vol. 15, No. 2, XP-000941161, Society for Industrial Microbiology, Fairfax, Virginia, US.
Fredricks DN, et al., "Changes in Vaginal Bacterial Concentrations with Intravaginal Metronidazole Therapy for Bacterial Vaginosis as Assembled by Quantitative PCR," Journal of Clinical Microbiology, Mar. 2009, pp. 721-726, vol. 47, No. 3, doi:10.1128/JCM.01384-08, American Society for Microbiology, Washington DC, US.
Fredricks DN, et al., "Targeted PCR for Detection of Vaginal Bacteria Associated with Bacterial Vaginosis," Journal of Clinical Microbiology, Oct. 2007, pp. 3270-3276, vol. 45, No. 10, doi:10.1128/JMC.01272-07, American Society for Microbiology, Washington DC, US.
Fredricks DN, et al., "Molecular Identification of Bacteria Associated with Bacterial Vaginosis," The New England Journal of Medicine, Nov. 3, 2005, pp. 1899-1911, vol. 353, Massachusetts Medical Society, Waltham, Massachusetts, US.
Hale et al., "Bacteria Associated with Bacterial Vaginosis," The New England Journal of Medicine, Jan. 12, 2006, pp. 202-203, vol. 354, No. 2, Massachusetts Medical Society, Waltham, Massachusetts, US.
Kim YJ, et al., "The enrichment of a ruminal bacterium (Megasphaera elsdenii YJ-4) that produces the trans-10, cis-12 isomer of conjugated linoleic acid," Journal of Applied Microbiology, 2002, pp. 976-982, vol. 92, The Society for Applied Microbiology, Bedford, UK.
Lamont RF, et al., "The vaginal microbiome: new information about genital tract flora using molecular based techniques," BJOG, 2011, pp. 533-549, vol. 118, DOI: 10.1111/j.1471-0528.2010.02840.x, RCOG, Oxford, UK.

(Continued)

Primary Examiner — Samuel Woolwine
Assistant Examiner — Olayinka Oyeyemi
(74) Attorney, Agent, or Firm — Jeffrey E. Landes

(57) ABSTRACT

Disclosed are nucleic acid oligomers, including amplification oligomers, capture probes, and detection probes, for detection of a 16S rRNA or its encoding gene from bacterial species associated with bacterial vaginosis. Also disclosed are methods of specific nucleic acid amplification and detection using the disclosed oligomers, as well as corresponding reaction mixtures and kits.

18 Claims, 1 Drawing Sheet

(56) References Cited

OTHER PUBLICATIONS

Marrazzo et al., "Risks for Acquisition of Bacterial Vaginosis Among Women Who Report Sex with Women: a Cohort Study," PLoS One 5(6): e11139. doi:10.1371/journal.pone.0011139, 2010, Marrazzo et al.

Moya D., et al., "Effects of dietary changes and yeast culture (*Saccharomyces cerevisiae*) on rumen microbial fermentation of Holstein heifers," J. Anim. Sci. 2009, pp. 2874-2881, doi:10/2527/jas.2008-1446, American Socitey of Animal Science, Champaign, Illinois, US.

Ohnishi A., et al., "Develoment of a 16S rRNA Gene Primer and PCR-Restriction Fragment Length Polymorphism Method for Rapid Detection of Members of the Genus *Megasphaera* and Species-Level Identification," Applied and Environmental Microbiology, Aug. 2011, pp. 5533-5535, vol. 77, No. 15, doi:10.1128/AEM.00359-11, American Society for Microbiology, Washington DC, US.

Ouwerkerk D., et al. "Enumeration of Megasphaera elsdenii in rumen contens by real-time Taq nuclease assay," Journal of Applied Microbiology, 2002, pp. 753-758, vol. 92, The Society for Applied Microbiology, Bedford, UK.

Pepin J, et al., "The Complex Vaginal Flora of West African Women with Bacterial Vaginosis." PLoS One, Sep. 2011, vol. 6, No. 9, e25082. doi:10.1371/journal.pone.0025082, Pepin et al.

Satokari R, et al., "Detection of beer spoilage bacteria Megasphaera and Pectinatus by polymerase chain reaction and colorimetric microplate hybridization," International Journal of Food Microbiology, 1998, pp. 119-127, vol. 45, Elsevier, Inc., Philadelphia, Pennsylvania, US.

Stevenson DM, et al., "Dominance of Prevotella and low abundance of classical ruminal bacterial species in the bovine rumen revealed by relative quantification real-time PCR," Appl. Microbiol. Biotechnol., 2007, pp. 165-174, col. 75, doi:10.1007/S00253-006-0802-y, Springer-Verlag, Berlin, DE.

Database WPI, Week 201126, Thomson Scientific. London. GB; AN 2011-D59201, XP002678611, & JP 2011 067101 A (Univ Tokyo Nogyo Apr. 7, 2011 (Apr. 7, 2011)), abstract.

International Preliminary Report on Patentability, International Patent Application No. PCT/US2012/035019, issued Oct. 29, 2013.

* cited by examiner

```
AGAGTTTGATCCTGGCTCAGGACGAACGCTGGCGGCGTGCTTAACACATG
CAAGTCGAACGAGAAGAGATGAGAAGCTTGCTTCTTATCGATTCGAGTGG
CAAACGGGTGAGTAACGCGTAAGCAACCTGCCCTTCAGATGGGGACAACA
GCTGGAAACGGCTGCTAATACCGAATACGTTCTTTTTGTCGCATGGCAGA
GAGAAGAAAGGGAGGCTCTTCGGAGCTTTCGCTGAAGGAGGGGCTTGCGT
CTGATTAGCTAGTTGGAGGGGTAACGGCCCACCAAGGCGACGATCAGTAG
CCGGTCTGAGAGGATGAACGGCCACATTGGGACTGAGACACGGCCCAGAC
TCCTACGGGAGGCAGCAGTGGGGAATCTTCCGCAATGGACGAAAGTCTGA
CGGAGCAACGCCGCGTGAACGATGACGGCCTTCGGGTTGTAAAGTTCTGT
TATACGGGACGAATGGCGTACGACGGTCAATACCCGTCGTAAGTGACGGT
ACCGTAAGAGAAAGCCACGGCTAACTACGTGCCAGCAGCCGCGGTAATAC
GTAGGTGGCAAGCGTTGTCCGGAATTATTGGGCGTAAAGGGCGCGCAGGC
GGCGTCGTAAGTCGGTCTTAAAAGTGCGGGGCTTAACCCCGTGAGGGGAC
CGAAACTGCGATGCTAGAGTATCGGAGAGGAAAGCGGAATTCCTAGTGTA
GCGGTGAAATGCGTAGATATTAGGAGGAACACCAGTGGCGAAAGCGGCTT
TCTGGACGACAACTGACGCTGAGGCGCGAAAGCCAGGGGAGCAAACGGGA
TTAGATACCCCGGTAGTCCTGGCGGTAAACGATGGATACTAGGTGTAGGA
GGTATCGACCCCTTCTGTGCCGGAGTTAACGCAATAAGTATCCCNGCCTG
GGGAGTACGGCCGCAAAGGCTGAAACTCAAAGGAATTGACGGGGGCCCGC
ACAAGCGGTGGAGTATGTGGTTTAATTCGACGCACGCGAAGAACCTTACC
AAGCCTTGACATTGATTGCTATGGGTAGAGATACCCAGTTCCTCTTCGGA
GGACAAGAAAACAGGTGGTGCACGGCTGTCGTCAGCTCGTGTCGTGAGAT
GTTGGGTTAAGTCCCGCAACGAGCGCAACCCCTATCTTCTGTTACCAGCG
AGTTAAGTCGGGGACTCAGGAGAGACTGCCGCAGACAATGCGGAGGAAGG
CGGGGATGACGTCAAGTCATCATGCCCCTTATGGCTTGGGCTACACACGT
ACTACAATGGCTCTTAATAGAGGGAAGCGAAGGAGCGATCCGGAGCAAAC
CCCAAAAACAGAGTCCCAGTTCGGATTGCAGGCTGCAACTCGCCTGCATG
AAGCAGGAATCGCTAGTAATCGCAGGTCAGCATACTGCGGTGAATACGTT
CCCGGGCCTTGTACACACCGCCCGTCACACCACGAAAGTCATTCACACCC
GAAGCCGGTGAGGTAACCTTTTGGAGCCAGCCGTCGAAGGTGGGGCGAT
GATTGGGGTGAAGTCGTAACAAGGTAACCG
```

COMPOSITIONS AND METHODS FOR DETECTING BV-ASSOCIATED BACTERIAL NUCLEIC ACID

CROSS-REFERENCE TO RELATED APPLICATIONS

This application is a national stage entry of International Patent Application No. PCT/US2012/035019, filed Apr. 25, 2012, and claims priority under 35 U.S.C. §119(e) to U.S. Provisional App. No. 61/478,753 filed on Apr. 25, 2011, the entire contents of both are incorporated herein by reference.

BACKGROUND OF THE INVENTION

Bacterial vaginosis (BV) is a common condition affecting millions of women annually and associated with serious health problems such as preterm labor resulting in low birth weight, pelvic inflammatory disease, and increased risk of human immunodeficiency virus infection. See, e.g., Bodner-Adler et al., *Am. J. Obstet. Gynecol.* 189:139-47, 2003; Hillier et al., *Clin. Infect. Dis.* 20:Suppl 2:S276-S278, 1995; Peipert et al., *Am. J. Obstet. Gynecol.* 184:856-63, 2001; Hillier et al., *Am. J. Osbstet. Gynecol.* 175:435-41, 1996; Martin et al., *J. Infect. Dis.* 180:1863-1868, 1999; Sturm-Ramirez et al., *J. Infect. Dis.* 182:467-473, 2000. No single etiologic agent has been implicated as the cause of bacterial vaginosis, and the syndrome is currently considered to be a polymicrobial disorder that is characterized by depletion of vaginal *Lactobacillus* species that produce hydrogen peroxide and an increase in the quantity of several vaginal anaerobic bacteria. See, e.g., Eschenbach et al., *J. Clin. Microbiol.* 27:251-256, 1989; Fredricks et al., *J. Clin. Microbiol.* 47:721-726, 2009.

The more recent use of cultivation-independent analyses of 16S rRNA gene sequences has identified various, previously unrecognized species that are prevalent in the vaginal flora and appear to be associated with BV. See, e.g., Fredricks et al., *N. Engl. J. Med.* 353:1899-1911, 2005; Ferris et al., *J. Clin. Microbiol.* 45:1016-1018, 2007. Among these are species most closely related to *Megasphaera*. See, e.g., Fredricks et al., supra. Recent studies also suggest that *Megasphaera*-like bacteria play an important role in BV pathogenesis and may be suitable markers of disease and treatment response. See Fredricks et al., *J. Clin. Microbiol.* 47:721-726, 2009.

Accordingly, there is a need for compositions, kits, and methods for rapidly and accurately detecting the presence or abundance of *Megasphaera* in a specimen. Such compositions, kits, and methods would be particularly useful for the diagnosis of BV or for monitoring a patient's response to BV treatment. The present invention meets these and other needs.

SUMMARY OF THE INVENTION

In one aspect, the present invention provides a combination of at least two oligomers for detecting in a sample a *Megasphaera* sp. 16S rRNA or a gene encoding a *Megasphaera* sp. 16S rRNA. In some embodiments, for a first *Megasphaera* target region, the oligomer combination comprises a first amplification oligomer comprising a first target-hybridizing sequence that is from about 15 to about 25 contiguous nucleotides contained in the sequence of SEQ ID NO:34 and that includes at least the sequence of SEQ ID NO:28; and a second amplification oligomer comprising a second target-hybridizing sequence that is from about 15 to about 25 contiguous nucleotides contained in the sequence of SEQ ID NO:36 and that includes at least the sequence of SEQ ID NO:35. In other embodiments, for a second *Megasphaera* target region, the oligomer combination comprises a first amplification oligomer comprising a first target-hybridizing sequence that is from about 15 to about 25 contiguous nucleotides contained in the sequence of SEQ ID NO:38 and that includes at least the sequence of SEQ ID NO:37; and a second amplification oligomer comprising a second target-hybridizing that is from about 15 to about 25 contiguous nucleotides contained in the sequence of SEQ ID NO:40 and that includes at least the sequence of SEQ ID NO:39.

In certain embodiments of the oligomer combination for the first *Megasphaera* target region, the first target-hybridizing sequence is contained in the sequence of SEQ ID NO:29 and/or the second target-hybridizing sequence is contained in the sequence of SEQ ID NO:33. The second target-hybridizing sequence may include at least the sequence of SEQ ID NO:32. Particularly suitable target-hybridizing sequences include SEQ ID NO:13 and SEQ ID NO:14 for the first amplification oligomer and SEQ ID NO:19 and SEQ ID NO:20 for the second amplification oligomer.

In certain embodiments of the oligomer combination for the second *Megasphaera* target region, the first target-hybridizing sequence has the sequence shown in SEQ ID NO:15 and/or the second target hybridizing sequence has the sequence shown in SEQ ID NO:21.

In some variations, the second amplification oligomer is a promoter primer further comprising a promoter sequence located 5' to the target-hybridizing sequence. Suitable promoter sequences include T7 RNA polymerase promoter sequences such as, e.g., the sequence shown in SEQ ID NO:22. In more specific embodiments, for the first *Megasphaera* target region, the second amplification oligomer has the sequence shown in SEQ ID NO:16 or SEQ ID NO:17; or for the second *Megasphaera* target region, the second amplification oligomer has the sequence shown in SEQ ID NO:18.

An oligomer combination may further include at least one capture probe oligomer. In some such embodiments, the capture probe oligomer includes a target-hybridizing sequence covalently attached to a sequence or moiety that binds to an immobilized probe. Suitable target-hybridizing sequences include the sequences shown in SEQ ID NOs:7-12. In particular variations, the capture probe oligomer has a sequence selected from SEQ ID NOs:1-6.

An oligomer combination may also include at least one detection probe oligomer. In certain embodiments for the first *Megasphaera* target region, the detection probe oligomer includes a target-hybridizing sequence that is from about 14 to about 40 nucleotides in length and is configured to specifically hybridize to a target sequence contained within SEQ ID NO:45 from about nucleotide position 290 to about nucleotide position 334. In some such embodiments, the detection probe target-hybridizing sequence is contained in the sequence of SEQ ID NO:31 and includes at least the sequence of SEQ ID NO:30. In specific variations, the detection probe target-hybridizing sequence for the first *Megasphaera* target region is selected from SEQ ID NO:23 and SEQ ID NO:25.

In certain embodiments comprising a detection probe oligomer for the second *Megasphaera* target region, the detection probe oligomer includes a target-hybridizing sequence that is from about 14 to about 40 nucleotides in length and is configured to specifically hybridize to a target sequence contained within SEQ ID NO:45 from about nucleotide position 466 to about nucleotide position 536 or 607. In some such embodiments, the detection probe target-hybridizing sequence is contained in the sequence of SEQ ID NO:24 and includes at least the sequence of SEQ ID NO:26. In specific variations, the detection probe target-hybridizing sequence for the second *Megasphaera* target region is selected from SEQ ID NO:24 and SEQ ID NO:26.

In yet other embodiments, an oligomer combination further comprises a pseudotarget oligomer that can be amplified using the first and second amplification oligomers. For example, in some variations for the first *Megasphaera* target region, the pseudotarget has the sequence shown in SEQ ID NO:27. In other variations for the second *Megasphaera* target region, the pseudotarget oligomer has the sequence shown in SEQ ID NO:41, SEQ ID NO:42, SEQ ID NO:43, or SEQ ID NO:44.

In others aspects, the present invention provides a kit or a reaction mixture comprising the combination of at least two oligomers as above.

In yet another aspect, the present invention provides a method for detecting, in a sample, a *Megasphaera* sp. target nucleic acid, wherein the target nucleic acid is a *Megasphaera* sp. 16S rRNA or a gene encoding the 16S rRNA. The method generally includes the following steps:
  (a) providing a sample suspected of containing a *Megasphaera* sp. bacterium;
  (b) contacting the sample with at least two oligomers for amplifying a *Megasphaera* sp. nucleic acid target region corresponding to the target nucleic acid, the oligomer combination comprising (i) for a first *Megasphaera* target region, a first amplification oligomer comprising a first target-hybridizing sequence that is from about 15 to about 25 contiguous nucleotides contained in the sequence of SEQ ID NO:34 and that includes at least the sequence of SEQ ID NO:28, and a second amplification oligomer comprising a second target-hybridizing sequence that is from about 15 to about 25 contiguous nucleotides contained in the sequence of SEQ ID NO:36 and that includes at least the sequence of SEQ ID NO:35; or (ii) for a second *Megasphaera* target region, a first amplification oligomer comprising a first target-hybridizing sequence that is from about 15 to about 25 contiguous nucleotides contained in the sequence of SEQ ID NO:38 and that includes at least the sequence of SEQ ID NO:37, and a second amplification oligomer comprising a second target-hybridizing that is from about 15 to about 25 contiguous nucleotides contained in the sequence of SEQ ID NO:40 and that includes at least the sequence of SEQ ID NO:39;
  (c) performing an in vitro nucleic acid amplification reaction, where any *Megasphaera* target nucleic acid present in the sample is used as a template for generating an amplification product; and
  (d) detecting the presence or absence of the amplification product, thereby indicating the presence or absence of *Megasphaera* sp. in said sample.

In certain embodiments of the method for the first *Megasphaera* target region, the first target-hybridizing sequence is contained in the sequence of SEQ ID NO:29 and/or the second target-hybridizing sequence is contained in the sequence of SEQ ID NO:33. The second target-hybridizing sequence may include at least the sequence of SEQ ID NO:32. Particularly suitable target-hybridizing sequences include SEQ ID NO:13 and SEQ ID NO:14 for the first amplification oligomer and SEQ ID NO:19 and SEQ ID NO:20 for the second amplification oligomer.

In certain embodiments of the method for the second *Megasphaera* target region, the first target-hybridizing sequence has the sequence shown in SEQ ID NO:15 and/or the second target hybridizing sequence has the sequence shown in SEQ ID NO:21.

In some variations of the method, the second amplification oligomer is a promoter primer further comprising a promoter sequence located 5' to the target-hybridizing sequence. Suitable promoter sequences include T7 RNA polymerase promoter sequences such as, e.g., the sequence shown in SEQ ID NO:22. In more specific embodiments, for the first *Megasphaera* target region, the second amplification oligomer has the sequence shown in SEQ ID NO:16 or SEQ ID NO:17; or for the second *Megasphaera* target region, the second amplification oligomer has the sequence shown in SEQ ID NO:18.

Typically, the method for detecting the *Megasphaera* target nucleic acid further comprising purifying the *Megasphaera* target nucleic acid from other components in the sample before the amplification step (b). In particular embodiments, the purifying step includes contacting the sample with at least one capture probe oligomer comprising a target-hybridizing sequence covalently attached to a sequence or moiety that binds to an immobilized probe. Suitable target-hybridizing sequences include the sequences shown in SEQ ID NOs:7-12. In particular variations, the capture probe oligomer has a sequence selected from SEQ ID NOs:1-6.

In some embodiments, the detecting step (d) includes contacting the in vitro nucleic acid amplification reaction with a detection probe oligomer configured to specifically hybridize to the amplification product under conditions whereby the presence or absence of the amplification product is determined, thereby indicating the presence or absence of *Megasphaera* sp. in the sample. In particular embodiments for the first *Megasphaera* target region, the detection probe oligomer includes a target-hybridizing sequence that is from about 14 to about 40 nucleotides in length and is configured to specifically hybridize to a target sequence contained within SEQ ID NO:45 from about nucleotide position 290 to about nucleotide position 334. In some such embodiments, the detection probe target-hybridizing sequence is contained in the sequence of SEQ ID NO:31 and includes at least the sequence of SEQ ID NO:30. In specific variations, the detection probe target-hybridizing sequence for the first *Megasphaera* target region is selected from SEQ ID NO:23 and SEQ ID NO:25.

In particular embodiments comprising use of a detection probe oligomer for the second *Megasphaera* target region, the detection probe oligomer includes a target-hybridizing sequence that is from about 14 to about 40 nucleotides in length and is configured to specifically hybridize to a target sequence contained within SEQ ID NO:45 from about nucleotide position 466 to about nucleotide position 536 or 607. In some such embodiments, the detection probe target-hybridizing sequence is contained in the sequence of SEQ ID NO:24 and includes at least the sequence of SEQ ID NO:26. In specific variations, the detection probe target-hybridizing sequence for the second *Megasphaera* target region is selected from SEQ ID NO:24 and SEQ ID NO:26.

In some embodiments of a method utilizing a detection probe oligomer, the detection probe includes at least one label. In specific variations, the one or more label(s) are selected from a chemiluminescent label, a fluorescent label, a quencher, or any combination thereof.

In other embodiments of a method utilizing a detection probe oligomer, the detecting step (d) occurs during the amplifying step (c). In some such embodiments, the detection probe comprises a fluorescent label, a quencher, or both (e.g., a TaqMan detection probe or a molecular beacon).

In still other embodiments of a method utilizing a detection probe oligomer, the detection probe further comprises a non-target-hybridizing sequence. In particular variations, the detection probe comprising a non-target-hybridizing sequence is a hairpin detection probe such as, e.g., a molecular beacon or a molecular torch.

In certain embodiments of the method for detecting the *Megasphaera* target nucleic acid, the amplification reaction at step (c) is an isothermal amplification reaction or a PCR amplification reaction. In specific variations, the amplification reaction is a real-time amplification reaction.

In yet other embodiments, the method for detecting the *Megasphaera* target nucleic acid further includes contacting the sample with a pseudotarget oligomer that can be amplified, using the first and second amplification oligomers, in the in vitro nucleic acid amplification reaction to generate a second amplification product that does not specifically hybridize to the detection probe under the detection reaction conditions. In some variations for the first *Megasphaera* target region, the pseudotarget has the sequence shown in SEQ ID NO:27. In other variations for the second *Megasphaera* target region, the pseudotarget oligomer has the sequence shown in SEQ ID NO:41, SEQ ID NO:42, SEQ ID NO:43, or SEQ ID NO:44.

In still another aspect, the present invention provides a detection probe oligomer for detecting a *Megasphaera* sp. target nucleic acid. In some embodiments, the detection probe oligomer comprises a target-hybridizing sequence that is from about 14 to about 40 nucleotides in length and is configured to specifically hybridize to a target sequence contained within SEQ ID NO:45 from about nucleotide position 290 to about nucleotide position 334. In some such embodiments, the detection probe target-hybridizing sequence is contained in the sequence of SEQ ID NO:31 and includes at least the sequence of SEQ ID NO:30. In specific variations, the detection probe target-hybridizing sequence for the first *Megasphaera* target region is selected from SEQ ID NO:23 and SEQ ID NO:25.

In other embodiments, a detection probe oligomer for detecting a *Megasphaera* sp. target nucleic acid comprises a target-hybridizing sequence that is from about 14 to about 40 nucleotides in length and is configured to specifically hybridize to a target sequence contained within SEQ ID NO:45 from about nucleotide position 466 to about nucleotide position 536 or 607. In some such embodiments, the detection probe target-hybridizing sequence is contained in the sequence of SEQ ID NO:24 and includes at least the sequence of SEQ ID NO:26. In specific variations, the detection probe target-hybridizing sequence for the second *Megasphaera* target region is selected from SEQ ID NO:24 and SEQ ID NO:26.

In some embodiments of a detection probe oligomer, the detection probe includes at least one label. In specific variations, the one or more label(s) are selected from a chemiluminescent label, a fluorescent label, a quencher, or any combination thereof. In more specific variations the detection probe comprises a fluorescent label and a quencher (e.g., a TaqMan detection probe or a molecular beacon).

In other embodiments of a detection probe oligomer, the detection probe further comprises a non-target-hybridizing sequence. In particular variations, the detection probe comprising a non-target-hybridizing sequence is a hairpin detection probe such as, e.g., a molecular beacon or a molecular torch.

These and other aspects of the invention will become evident upon reference to the following detailed description of the invention and the attached drawings.

DEFINITIONS

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise.

The terms "a," "an," and "the" include plural referents, unless the context clearly indicates otherwise. For example, "a nucleic acid" as used herein is understood to represent one or more nucleic acids. As such, the terms "a" (or "an"), "one or more," and "at least one" can be used interchangeably herein.

"Sample" includes any specimen that may contain *Megasphaera* sp. (e.g., *Megasphaera elsdenii*) or components thereof, such as nucleic acids or fragments of nucleic acids. Samples include "biological samples" which include any tissue or material derived from a living or dead human that may contain *Megasphaera* sp. or target nucleic acid derived therefrom, including, e.g., vaginal swab samples, cervical brush samples, respiratory tissue or exudates such as bronchoscopy, bronchoalveolar lavage (BAL) or lung biopsy, sputum, saliva, peripheral blood, plasma, serum, lymph node, gastrointestinal tissue, feces, urine, semen or other body fluids or materials. The biological sample may be treated to physically or mechanically disrupt tissue or cell structure, thus releasing intracellular components into a solution which may further contain enzymes, buffers, salts, detergents and the like, which are used to prepare, using standard methods, a biological sample for analysis. Also, samples may include processed samples, such as those obtained from passing samples over or through a filtering device, or following centrifugation, or by adherence to a medium, matrix, or support.

"Nucleic acid" refers to a multimeric compound comprising two or more covalently bonded nucleosides or nucleoside analogs having nitrogenous heterocyclic bases, or base analogs, where the nucleosides are linked together by phosphodiester bonds or other linkages to form a polynucleotide. Nucleic acids include RNA, DNA, or chimeric DNA-RNA polymers or oligonucleotides, and analogs thereof. A nucleic acid "backbone" may be made up of a variety of linkages, including one or more of sugar-phosphodiester linkages, peptide-nucleic acid bonds (in "peptide nucleic acids" or PNAs, see, e.g., International Patent Application Pub. No. WO 95/32305), phosphorothioate linkages, methylphosphonate linkages, or combinations thereof. Sugar moieties of the nucleic acid may be either ribose or deoxyribose, or similar compounds having known substitutions such as, for example, 2'-methoxy substitutions and 2'-halide substitutions (e.g., 2'-F). Nitrogenous bases may be conventional bases (A, G, C, T, U), analogs thereof (e.g., inosine, 5-methylisocytosine, isoguanine; see, e.g., *The Biochemistry of the Nucleic Acids* 5-36, Adams et al., ed., 11th ed., 1992; Abraham et al., 2007, *Bio Techniques* 43: 617-24), which include derivatives of purine or pyrimidine bases (e.g., $N^4$-methyl deoxygaunosine, deaza- or aza-purines, deaza- or aza-pyrimidines, pyrimidine bases having substituent groups at the 5 or 6 position, purine bases having an altered or replacement substituent at the 2, 6 and/or 8 position, such as 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines, and pyrazolo-compounds, such as unsubstituted or 3-substituted pyrazolo [3,4-d]pyrimidine; U.S. Pat. Nos. 5,378,825, 6,949,367 and International Patent Application Pub. No. WO 93/13121, each incorporated by reference herein). Nucleic acids may include "abasic" residues in which the backbone does not include a nitrogenous base for one or more residues (see, e.g., U.S. Pat. No. 5,585,481, incorporated by reference herein). A nucleic acid may comprise only conventional sugars, bases, and linkages as found in RNA and DNA, or may include conventional components and substitutions (e.g., conventional bases linked by a 2'-methoxy backbone, or a nucleic acid including a mixture of conventional bases and one or more base analogs). Nucleic acids may include "locked nucleic acids" (LNA), in which one or more nucleotide monomers have a bicyclic furanose unit locked in an RNA mimicking sugar conformation, which enhances hybridization affinity toward complementary sequences in single-stranded RNA (ssRNA), single-stranded DNA (ssDNA), or double-stranded DNA (dsDNA) (Vester et al., *Biochemistry* 43:13233-41, 2004, incorporated by reference herein). Nucleic acids may include modified bases to alter the function or behavior of the nucleic acid, e.g., addition of a 3'-terminal dideoxynucleotide to block additional nucleotides from being added to the nucleic acid. Synthetic methods for making nucleic acids in vitro are well known in the art although nucleic acids may be purified from natural sources using routine techniques.

The term "polynucleotide" as used herein denotes a nucleic acid chain. Throughout this application, nucleic acids are designated by the 5'-terminus to the 3'-terminus. Standard nucleic acids, e.g., DNA and RNA, are typically synthesized "3'-to-5'," i.e., by the addition of nucleotides to the 5'-terminus of a growing nucleic acid.

A "nucleotide" as used herein is a subunit of a nucleic acid consisting of a phosphate group, a 5-carbon sugar and a nitrogenous base. The 5-carbon sugar found in RNA is ribose. In DNA, the 5-carbon sugar is 2'-deoxyribose. The term also includes analogs of such subunits, such as a methoxy group at the 2' position of the ribose (2'-O-Me). As used herein, methoxy oligonucleotides containing "T" residues have a methoxy group at the 2' position of the ribose moiety, and a uracil at the base position of the nucleotide.

A "non-nucleotide unit" as used herein is a unit that does not significantly participate in hybridization of a polymer. Such units must not, for example, participate in any significant hydrogen bonding with a nucleotide, and would exclude units having as a component one of the five nucleotide bases or analogs thereof.

A "target nucleic acid" as used herein is a nucleic acid comprising a target sequence to be amplified. Target nucleic acids may be DNA or RNA as described herein, and may be either single-stranded or double-stranded. The target nucleic acid may include other sequences besides the target sequence, which may not be amplified. Typical target nucleic acids include virus genomes, bacterial genomes, fungal genomes, plant genomes, animal genomes, rRNA, tRNA, or mRNA from viruses, bacteria or eukaryotic cells, mitochondrial DNA, or chromosomal DNA.

By "isolated" it is meant that a sample containing a target nucleic acid is taken from its natural milieu, but the term does not connote any degree of purification.

The term "target sequence" as used herein refers to the particular nucleotide sequence of the target nucleic acid that is to be amplified and/or detected. The "target sequence" includes the complexing sequences to which oligonucleotides (e.g., priming oligonucleotides and/or promoter oligonucleotides) complex during an amplification processes (e.g., TMA). Where the target nucleic acid is originally single-stranded, the term "target sequence" will also refer to the sequence complementary to the "target sequence" as present in the target nucleic acid. Where the target nucleic acid is originally double-stranded, the term "target sequence" refers to both the sense (+) and antisense (−) strands. In choosing a target sequence, the skilled artisan will understand that a "unique" sequence should be chosen so as to distinguish between unrelated or closely related target nucleic acids.

"Target-hybridizing sequence" is used herein to refer to the portion of an oligomer that is configured to hybridize with a target nucleic acid sequence. Preferably, the target-hybridizing sequences are configured to specifically hybridize with a target nucleic acid sequence. Target-hybridizing sequences may be 100% complementary to the portion of the target sequence to which they are configured to hybridize; but not necessarily. Target-hybridizing sequences may also include inserted, deleted and/or substituted nucleotide residues relative to a target sequence. Less than 100% complementarity of a target-hybridizing sequence to a target sequence may arise, for example, when the target nucleic acid is a plurality strains within a species, such as would be the case for an oligomer configured to hybridize to the various strains of *Megasphaera*. It is understood that other reasons exist for configuring a target-hybridizing sequence to have less than 100% complementarity to a target nucleic acid.

Oligomer target-hybridizing sequences defined herein by reference to a specific sequence (e.g., by reference a region within SEQ ID NO:45) are also understood to include functional complements thereof, unless the context clearly dictates otherwise. Thus, for example, where target-hybridizing regions of first and second amplification oligomers are defined by reference to specific sequences corresponding, respectively, to sense and antisense strands of a target nucleic acid, it is understood that the amplification oligomer combination may include a functional combination of first and second amplification oligomers having target-hybridizing sequences that are the respective complements of the specific reference sequences. Similarly, and again by way of example, where a target-hybridizing sequence for a detection probe oligomer is defined reference to a specific sequence, it is understood that the detection probe may include a corresponding detection probe oligomer having a target-hybridizing sequence that is the complement of the specific reference sequence; or where a detection probe oligomer is defined by its configuration to hybridize to a specific sequence, it is understood that the detection probe may include a corresponding detection probe oligomer having a target-hybridizing sequence that is configured to hybridize to the complement of the specific reference sequence.

The term "targets a sequence" as used herein in reference to a region of *Megasphaera* nucleic acid refers to a process whereby an oligonucleotide hybridizes to the target sequence in a manner that allows for amplification and detection as described herein. In one preferred embodiment, the oligonucleotide is complementary with the targeted *Megasphaera* nucleic acid sequence and contains no mismatches. In another preferred embodiment, the oligonucleotide is complementary but contains 1, 2, 3, 4, or 5 mismatches with the targeted *Megasphaera* nucleic acid sequence. Preferably, the oligonucleotide that hybridizes to the *Megasphaera* nucleic acid sequence includes at least 10 to as many as 50 nucleotides complementary to the target sequence. It is understood that at least 10 and as many as 50 is an inclusive range such that 10, 50 and each whole number there between are included. Preferably, the oligomer specifically hybridizes to the target sequence.

The term "configured to" denotes an actual arrangement of the polynucleotide sequence configuration of a referenced oligonucleotide target-hybridizing sequence. For example, amplification oligomers that are configured to generate a specified amplicon from a target sequence have polynucleotide sequences that hybridize to the target sequence and can be used in an amplification reaction to generate the amplicon. Also as an example, oligonucleotides that are configured to specifically hybridize to a target sequence have a polynucleotide sequence that specifically hybridizes to the referenced sequence under stringent hybridization conditions.

The term "configured to specifically hybridize to" as used herein means that the target-hybridizing region of an amplification oligonucleotide, detection probe, or other oligonucleotide is designed to have a polynucleotide sequence that could target a sequence of the referenced *Megasphaera* target region. Such an oligonucleotide is not limited to targeting that sequence only, but is rather useful as a composition, in a kit or in a method for targeting a *Megasphaera* target nucleic acid. The oligonucleotide is designed to function as a component of an assay for amplification and detection of *Megasphaera* from a sample, and therefore is designed to target *Megasphaera* in the presence of other nucleic acids commonly found in testing samples. "Specifically hybridize to" does not mean exclusively hybridize to, as some small level of hybridization to non-target nucleic acids may occur, as is understood in the art. Rather, "specifically hybridize to" means that the oligonucleotide is configured to function in an assay to primarily hybridize the target so that an accurate detection of target nucleic acid in a sample can be determined. The term "configured to" denotes an actual arrangement of the polynucleotide sequence configuration of the amplification oligonucleotide target-hybridizing sequence.

The term "fragment," as used herein in reference to the *Megasphaera* targeted nucleic acid, refers to a piece of contiguous nucleic acid. In certain embodiments, the fragment includes contiguous nucleotides from a *Megasphaera* 16S ribosomal RNA, wherein the number of 16S contiguous nucleotides in the fragment are less than that for the entire 16S.

The term "region," as used herein, refers to a portion of a nucleic acid wherein said portion is smaller than the entire nucleic acid. For example, when the nucleic acid in reference is an oligonucleotide promoter primer, the term "region" may be used refer to the smaller promoter portion of the entire oligonucleotide. Similarly, and also as example only, when the nucleic acid is a 16S ribosomal RNA, the term "region" may be used to refer to a smaller area of the nucleic acid, wherein the smaller area is targeted by one or more oligonucleotides of the invention. As another non-limiting example, when the nucleic acid in reference is an amplicon, the term region may be used to refer to the smaller nucleotide sequence identified for hybridization by the target-hybridizing sequence of a probe.

The interchangeable terms "oligomer," "oligo," and "oligonucleotide" refer to a nucleic acid having generally less than 1,000 nucleotide (nt) residues, including polymers in a range having a lower limit of about 5 nt residues and an upper limit of about 500 to 900 nt residues. In some embodiments, oligonucleotides are in a size range having a lower limit of about 12 to 15 nt and an upper limit of about 50 to 600 nt, and other embodiments are in a range having a lower limit of about 15 to 20 nt and an upper limit of about 22 to 100 nt. Oligonucleotides may be purified from naturally occurring sources or may be synthesized using any of a variety of well-known enzymatic or chemical methods. The term oligonucleotide does not denote any particular function to the reagent; rather, it is used generically to cover all such reagents described herein. An oligonucleotide may serve various different functions. For example, it may function as a primer if it is specific for and capable of hybridizing to a complementary strand and can further be extended in the presence of a nucleic acid polymerase; it may function as a primer and provide a promoter if it contains a sequence recognized by an RNA polymerase and allows for transcription (e.g., a T7 Primer); and it may function to detect a target nucleic acid if it is capable of hybridizing to the target nucleic acid, or an amplicon thereof, and further provides a detectable moiety (e.g., an acridinium-ester compound).

As used herein, an ° oligonucleotide "substantially corresponding to" a specified reference nucleic acid sequence means that the oligonucleotide is sufficiently similar to the reference nucleic acid sequence such that the oligonucleotide has similar hybridization properties to the reference nucleic acid sequence in that it would hybridize with the same target nucleic acid sequence under stringent hybridization conditions. One skilled in the art will understand that "substantially corresponding oligonucleotides" can vary from a reference sequence and still hybridize to the same target nucleic acid sequence. It is also understood that a first nucleic acid corresponding to a second nucleic acid includes the RNA and DNA thereof and includes the complements thereof, unless the context clearly dictates otherwise. This variation from the nucleic acid may be stated in terms of a percentage of identical bases within the sequence or the percentage of perfectly complementary bases between the probe or primer and its target sequence. Thus, in certain embodiments, an oligonucleotide "substantially corresponds" to a reference nucleic acid sequence if these percentages of base identity or complementarity are from 100% to about 80%. In preferred embodiments, the percentage is from 100% to about 85%. In more preferred embodiments, this percentage is from 100% to about 90%; in other preferred embodiments, this percentage is from 100% to about 95%. Similarly, a region of a nucleic acid or amplified nucleic acid can be referred to herein as corresponding to a reference nucleic acid sequence. One skilled in the art will understand the various modifications to the hybridization conditions that might be required at various percentages of complementarity to allow hybridization to a specific target sequence without causing an unacceptable level of non-specific hybridization.

A "helper oligonucleotide" or "helper" refers to an oligonucleotide designed to bind to a target nucleic acid and impose a different secondary and/or tertiary structure on the target to increase the rate and extent of hybridization of a detection probe or other oligonucleotide with the targeted nucleic acid, as described, for example, in U.S. Pat. No. 5,030,557, incorporated by reference herein. Helpers may also be used to assist with the target hybridization and function of primer, target capture and other oligonucleotides.

As used herein, a "blocking moiety" is a substance used to "block" the 3'-terminus of an oligonucleotide or other nucleic acid so that it cannot be efficiently extended by a nucleic acid polymerase. Oligomers not intended for extension by a nucleic acid polymerase may include a blocker group that replaces the 3'OH to prevent enzyme-mediated extension of the oligomer in an amplification reaction. For example, blocked amplification oligomers and/or detection probes present during amplification may not have functional 3'OH and instead include one or more blocking groups located at or near the 3' end. In some embodiments a blocking group near the 3' end and may be within five residues of the 3' end and is sufficiently large to limit binding of a polymerase to the oligomer. In other embodiments a blocking group is covalently attached to the 3' terminus. Many different chemical groups may be used to block the 3' end, e.g., alkyl groups, non-nucleotide linkers, alkane-diol dideoxynucleotide residues, and cordycepin.

An "amplification oligomer" is an oligomer, at least the 3'-end of which is complementary to a target nucleic acid, and which hybridizes to a target nucleic acid, or its complement, and participates in a nucleic acid amplification reaction. An example of an amplification oligomer is a "primer" that hybridizes to a target nucleic acid and contains a 3' OH end that is extended by a polymerase in an amplification process. Another example of an amplification oligomer is an oligomer that is not extended by a polymerase (e.g., because it has a 3' blocked end) but participates in or facilitates amplification. For example, the 5' region of an amplification oligonucleotide may include a promoter sequence that is non-complementary to the target nucleic acid (which may be referred to as a "promoter primer" or "promoter provider"). Those skilled in the art will understand that an amplification oligomer that functions as a primer may be modified to include a 5' promoter sequence, and thus function as a promoter primer. Incorporating a 3' blocked end further modifies the promoter primer, which is now capable of hybridizing to a target nucleic acid and providing an upstream promoter sequence that serves to initiate transcription, but does not provide a primer for oligo extension. Such a modified oligo is referred to herein as a "promoter provider" oligomer. Size ranges for amplification oligonucleotides include those that are about 10 to about 70 nt long (not including any promoter sequence or poly-A tails) and contain at least about 10 contiguous bases, or even at least 12 contiguous bases that are complementary to a region of the target nucleic acid sequence (or a complementary strand thereof). The contiguous bases are at least 80%, or at least 90%, or completely complementary to the target sequence to which the amplification oligomer binds. An amplification oligomer may optionally include modified nucleotides or analogs, or additional nucleotides that participate in an amplification reaction but are not complementary to or contained in the target nucleic acid, or template sequence. It is understood that when referring to ranges for the length of an oligonucleotide, amplicon, or other nucleic acid, that the range is inclusive of all whole numbers (e.g., 19-25 contiguous nucleotides in length includes 19, 20, 21, 22, 23, 24 & 25).

As used herein, a "promoter" is a specific nucleic acid sequence that is recognized by a DNA-dependent RNA polymerase ("transcriptase") as a signal to bind to the nucleic acid and begin the transcription of RNA at a specific site.

As used herein, a "promoter provider" or "provider" refers to an oligonucleotide comprising first and second regions, and which is modified to prevent the initiation of DNA synthesis from its 3'-terminus. The "first region" of a promoter provider oligonucleotide comprises a base sequence which hybridizes to a DNA template, where the hybridizing sequence is situated 3', but not necessarily adjacent to, a promoter region. The hybridizing portion of a promoter oligonucleotide is typically at least 10 nucleotides in length, and may extend up to 50 or more nucleotides in length. The "second region" comprises a promoter sequence for an RNA polymerase. A promoter oligonucleotide is engineered so that it is incapable of being extended by an RNA- or DNA-dependent DNA polymerase, e.g., reverse transcriptase, preferably comprising a blocking moiety at its 3'-terminus as described above. As referred to herein, a "T7 Provider" is a blocked promoter provider oligonucleotide that provides an oligonucleotide sequence that is recognized by T7 RNA polymerase.

As used herein, a "terminating oligonucleotide" or "blocker oligonucleotide" is an oligonucleotide comprising a base sequence that is complementary to a region of the target nucleic acid in the vicinity of the 5'-end of the target sequence, so as to "terminate" primer extension of a nascent nucleic acid that includes a priming oligonucleotide, thereby providing a defined 3'-end for the nascent nucleic acid strand.

An "extender oligomer" or "extend oligomer" as used herein refers to an oligonucleotide that is the same sense as the T7 Provider and may act as a helper oligonucleotide that opens up structure or improves specificity.

"Amplification" refers to any known procedure for obtaining multiple copies of a target nucleic acid sequence or its complement or fragments thereof. The multiple copies may be referred to as amplicons or amplification products. Amplification of "fragments" refers to production of an amplified nucleic acid that contains less than the complete target nucleic acid or its complement, e.g., produced by using an amplification oligonucleotide that hybridizes to, and initiates polymerization from, an internal position of the target nucleic acid. Known amplification methods include, for example, replicase-mediated amplification, polymerase chain reaction (PCR), ligase chain reaction (LCR), strand-displacement amplification (SDA), and transcription-mediated or transcription-associated amplification. Replicase-mediated amplification uses self-replicating RNA molecules, and a replicase such as QB-replicase (see, e.g., U.S. Pat. No. 4,786,600, incorporated by reference herein). PCR amplification uses a DNA polymerase, pairs of primers, and thermal cycling to synthesize multiple copies of two complementary strands of dsDNA or from a cDNA (see, e.g., U.S. Pat. Nos. 4,683,195; 4,683,202; and 4,800,159; each incorporated by reference herein). LCR amplification uses four or more different oligonucleotides to amplify a target and its complementary strand by using multiple cycles of hybridization, ligation, and denaturation (see, e.g., U.S. Pat. Nos. 5,427,930 and 5,516,663, each incorporated by reference herein). SDA uses a primer that contains a recognition site for a restriction endonuclease and an endonuclease that nicks one strand of a hemimodified DNA duplex that includes the target sequence, whereby amplification occurs in a series of primer extension and strand displacement steps (see, e.g., U.S. Pat. Nos. 5,422,252; 5,547,861; and 5,648,211; each incorporated by reference herein).

"Transcription-associated amplification" or "transcription-mediated amplification" (TMA) refer to nucleic acid amplification that uses an RNA polymerase to produce multiple RNA transcripts from a nucleic acid template. These methods generally employ an RNA polymerase, a DNA polymerase, deoxyribonucleoside triphosphates, ribonucleoside triphosphates, and a template complementary oligonucleotide that includes a promoter sequence, and optionally may include one or more other oligonucleotides. TMA methods and single-primer transcription associated amplification method are embodiments of amplification methods used for detection of *Megasphaera* target sequences as described herein. Variations of transcription-associated amplification are well known in the art as previously disclosed in detail (see, e.g., U.S. Pat. Nos. 4,868,105; 5,124,246; 5,130,238; 5,399,491; 5,437,990; 5,554,516; and 7,374,885; and International Patent Application Pub. Nos. WO 88/01302; WO 88/10315; and WO 95/03430; each incorporated by reference herein). The person of ordinary skill in the art will appreciate that the disclosed compositions may be used in amplification methods based on extension of oligomer sequences by a polymerase.

As used herein, the term "real-time TMA" refers to single-primer transcription-mediated amplification ("TMA") of target nucleic acid that is monitored by real-time detection means.

The term "amplicon" or the term "amplification product" as used herein refers to the nucleic acid molecule generated during an amplification procedure that is complementary or homologous to a sequence contained within the target sequence. The complementary or homologous sequence of an amplicon is sometimes referred to herein as a "target-specific sequence." Amplicons generated using the amplification oligomers of the current invention may comprise non-target specific sequences. Amplicons can be double stranded or single stranded and can include DNA, RNA or both. For example, DNA-dependent RNA polymerase transcribes single stranded amplicons from double-stranded DNA during transcription-mediated amplification procedures. These single-stranded amplicons are RNA amplicons and can be either strand of a double-stranded complex, depending on how the amplification oligomers are configured. Thus, amplicons can be single-stranded RNA. RNA-dependent DNA polymerases synthesize a DNA strand that is complementary to an RNA template. Thus, amplicons can be double-stranded DNA and RNA hybrids. RNA-dependent DNA polymerases often include RNase activity, or are used in conjunction with an RNase, which degrades the RNA strand. Thus, amplicons can be single stranded DNA. RNA-dependent DNA polymerases and DNA-dependent DNA polymerases synthesize complementary DNA strands from DNA templates. Thus, amplicons can be double-stranded DNA. RNA-dependent RNA polymerases synthesize RNA from an RNA template. Thus, amplicons can be double-stranded RNA. DNA-dependent RNA polymerases synthesize RNA from double-stranded DNA templates, also referred to as transcription. Thus, amplicons can be single stranded RNA. Amplicons and methods for generating amplicons are known to those skilled in the art. For convenience herein, a single strand of RNA or a single strand of DNA may represent an amplicon generated by an amplification oligomer combination of the current invention. Such representation is not meant to limit the amplicon to the representation shown. Skilled artisans in possession of the instant disclosure will use amplification oligomers and polymerase enzymes to generate any of the numerous types of amplicons, all within the spirit and scope of the current invention.

A "non-target-specific sequence," as is used herein refers to a region of an oligomer sequence, wherein said region does not stably hybridize with a target sequence under standard hybridization conditions. Oligomers with non-target-specific sequences include, but are not limited to, promoter primers and molecular beacons. An amplification oligomer may contain a sequence that is not complementary to the target or template sequence; for example, the 5' region of a primer may include a promoter sequence that is non-complementary to the target nucleic acid (referred to as a "promoter primer"). Those skilled in the art will understand that an amplification oligomer that functions as a primer may be modified to include a 5' promoter sequence, and thus function as a promoter primer. Similarly, a promoter primer may be modified by removal of, or synthesis without, a promoter sequence and still function as a primer. A 3' blocked amplification oligomer may provide a promoter sequence and serve as a template for polymerization (referred to as a "promoter provider"). Thus, an amplicon that is generated by an amplification oligomer member such as a promoter primer will comprise a target-specific sequence and a non-target-specific sequence.

"Detection probe," "detection oligonucleotide," and "detection probe oligomer" are used interchangeably to refer to a nucleic acid oligomer that hybridizes specifically to a target sequence in a nucleic acid, or in an amplified nucleic acid, under conditions that promote hybridization to allow detection of the target sequence or amplified nucleic acid. Detection may either be direct (e.g., a probe hybridized directly to its target sequence) or indirect (e.g., a probe linked to its target via an intermediate molecular structure). Detection probes may be DNA, RNA, analogs thereof or combinations thereof and they may be labeled or unlabeled. Detection probes may further include alternative backbone linkages such as, e.g., 2'-O-methyl linkages. A detection probe's "target sequence" generally refers to a smaller nucleic acid sequence region within a larger nucleic acid sequence that hybridizes specifically to at least a portion of a probe oligomer by standard base pairing. A detection probe may comprise target-specific sequences and other sequences that contribute to the three-dimensional conformation of the probe (see, e.g., U.S. Pat. Nos. 5,118,801; 5,312,728; 6,849,412; 6,835,542; 6,534,274; and 6,361,945; and US Patent Application Pub. No. 20060068417; each incorporated by reference herein).

By "stable" or "stable for detection" is meant that the temperature of a reaction mixture is at least 2° C. below the melting temperature of a nucleic acid duplex.

As used herein, a "label" refers to a moiety or compound joined directly or indirectly to a probe that is detected or leads to a detectable signal. Direct labeling can occur through bonds or interactions that link the label to the probe, including covalent bonds or non-covalent interactions, e.g., hydrogen bonds, hydrophobic and ionic interactions, or formation of chelates or coordination complexes. Indirect labeling can occur through use of a bridging moiety or "linker" such as a binding pair member, an antibody or additional oligomer, which is either directly or indirectly labeled, and which may amplify the detectable signal. Labels include any detectable moiety, such as a radionuclide, ligand (e.g., biotin, avidin), enzyme or enzyme substrate, reactive group, or chromophore (e.g., dye, particle, or bead that imparts detectable color), luminescent compound (e.g., bioluminescent, phosphorescent, or chemiluminescent labels), or fluorophore. Labels may be detectable in a homogeneous assay in which bound labeled probe in a mixture exhibits a detectable change different from that of an unbound labeled probe, e.g., instability or differential degradation properties. A "homogeneous detectable label" can be detected without physically removing bound from unbound forms of the label or labeled probe (see, e.g., U.S. Pat. Nos. 5,283,174; 5,656,207; and 5,658,737; each incorporated by reference herein). Labels include chemiluminescent compounds, e.g., acridinium ester ("AE") compounds that include standard AE and derivatives (see, e.g., U.S. Pat. Nos. 5,656,207; 5,658,737; and 5,639,604; each incorporated by reference herein). Synthesis and methods of attaching labels to nucleic acids and detecting labels are well known. (See, e.g., Sambrook et al., *Molecular Cloning, A Laboratory Manual,* 2nd ed. (Cold Spring Harbor Laboratory Press, Cold Spring Harbor, N.Y., 1989), Chapter 10, incorporated by reference herein. See also U.S. Pat. Nos. 5,658,737; 5,656,207; 5,547,842; 5,283,174; and 4,581,333; each incorporated by reference herein). More than one label, and more than one type of label, may be present on a particular probe, or detection may use a mixture of probes in which each probe is labeled with a compound that produces a detectable signal (see, e.g., U.S. Pat. Nos. 6,180,340 and 6,350,579, each incorporated by reference herein).

"Capture probe," "capture oligonucleotide," and "capture probe oligomer" are used interchangeably to refer to a nucleic acid oligomer that specifically hybridizes to a target sequence in a target nucleic acid by standard base pairing and joins to a binding partner on an immobilized probe to capture the target nucleic acid to a support. One example of a capture oligomer includes two binding regions: a sequence-binding region (e.g., target-specific portion) and an immobilized probe-binding region, usually on the same oligomer, although the two regions may be present on two different oligomers joined together by one or more linkers. Another embodiment of a capture oligomer uses a target-sequence binding region that includes random or non-random poly-GU, poly-GT, or poly U sequences to bind non-specifically to a target nucleic acid and link it to an immobilized probe on a support.

As used herein, an "immobilized oligonucleotide," "immobilized probe," or "immobilized nucleic acid" refers to a nucleic acid binding partner that joins a capture oligomer to a support, directly or indirectly. An immobilized probe joined to a support facilitates separation of a capture probe bound target from unbound material in a sample. One embodiment of an immobilized probe is an oligomer joined to a support that facilitates separation of bound target sequence from unbound material in a sample. Supports may include known materials, such as matrices and particles free in solution, which may be made of nitrocellulose, nylon, glass, polyacrylate, mixed polymers, polystyrene, silane, polypropylene, metal, or other compositions, of which one embodiment is magnetically attractable particles. Supports may be monodisperse magnetic spheres (e.g., uniform size±5%), to which an immobilized probe is joined directly (via covalent linkage, chelation, or ionic interaction), or indirectly (via one or more linkers), where the linkage or interaction between the probe and support is stable during hybridization conditions.

By "complementary" is meant that the nucleotide sequences of similar regions of two single-stranded nucleic acids, or to different regions of the same single-stranded nucleic acid have a nucleotide base composition that allow the single-stranded regions to hybridize together in a stable double-stranded hydrogen-bonded region under stringent hybridization or amplification conditions. Sequences that hybridize to each other may be completely complementary or partially complementary to the intended target sequence by standard nucleic acid base pairing (e.g., G:C, A:T or A:U pairing). By "sufficiently complementary" is meant a contiguous sequence that is capable of hybridizing to another sequence by hydrogen bonding between a series of complementary bases, which may be complementary at each position in the sequence by standard base pairing or may contain one or more residues, including abasic residues, that are not complementary. Sufficiently complementary contiguous sequences typically are at least 80%, or at least 90%, complementary to a sequence to which an oligomer is intended to specifically hybridize. Sequences that are "sufficiently complementary" allow stable hybridization of a nucleic acid oligomer with its target sequence under appropriate hybridization conditions, even if the sequences are not completely complementary. When a contiguous sequence of nucleotides of one single-stranded region is able to form a series of "canonical" hydrogen-bonded base pairs with an analogous sequence of nucleotides of the other single-stranded region, such that A is paired with U or T and C is paired with G, the nucleotides sequences are "completely" complementary (see, e.g., Sambrook et al., *Molecular Cloning, A Laboratory Manual, $2^{nd}$* ed. (Cold Spring Harbor Laboratory Press, Cold Spring Harbor, N.Y., 1989) at §§1.90-1.91, 7.37-7.57, 9.47-9.51 and 11.47-11.57, particularly §§9.50-9.51, 11.12-11.13, 11.45-11.47 and 11.55-11.57, incorporated by reference herein). It is understood that ranges for percent identity are inclusive of all whole and partial numbers (e.g., at least 90% includes 90, 91, 93.5, 97.687 and etc.).

By "preferentially hybridize" or "specifically hybridize" is meant that under stringent hybridization assay conditions, probes hybridize to their target sequences, or replicates thereof, to form stable probe:target hybrids, while at the same time formation of stable probe:non-target hybrids is minimized. Thus, a probe hybridizes to a target sequence or replicate thereof to a sufficiently greater extent than to a non-target sequence, to enable one having ordinary skill in the art to accurately quantitate the RNA replicates or complementary DNA (cDNA) of the target sequence formed during the amplification. Appropriate hybridization conditions are well-known in the art, may be predicted based on sequence composition, or can be determined by using routine testing methods (see, e.g., Sambrook et al., *Molecular Cloning, A Laboratory Manual, $2^{nd}$* ed. (Cold Spring Harbor Laboratory Press, Cold Spring Harbor, N.Y., 1989) at §§1.90-1.91, 7.37-7.57, 9.47-9.51 and 11.47-11.57, particularly §§9.50-9.51, 11.12-11.13, 11.45-11.47 and 11.55-11.57, incorporated by reference herein).

By "nucleic acid hybrid," "hybrid," or "duplex" is meant a nucleic acid structure containing a double-stranded, hydrogen-bonded region wherein each strand is complementary to the other, and wherein the region is sufficiently stable under stringent hybridization conditions to be detected by means including, but not limited to, chemiluminescent or fluorescent light detection, autoradiography, or gel electrophoresis. Such hybrids may comprise RNA:RNA, RNA:DNA, or DNA:DNA duplex molecules.

"Sample preparation" refers to any steps or method that treats a sample for subsequent amplification and/or detection of *Megasphaera* nucleic acids present in the sample. Samples may be complex mixtures of components of which the target nucleic acid is a minority component. Sample preparation may include any known method of concentrating components, such as microbes or nucleic acids, from a larger sample volume, such as by filtration of airborne or waterborne particles from a larger volume sample or by isolation of microbes from a sample by using standard microbiology methods. Sample preparation may include physical disruption and/or chemical lysis of cellular components to release intracellular components into a substantially aqueous or organic phase and removal of debris, such as by using filtration, centrifugation or adsorption. Sample preparation may include use of a nucleic acid oligonucleotide that selectively or non-specifically capture a target nucleic acid and separate it from other sample components (e.g., as described in U.S. Pat. No. 6,110,678 and International Patent Application Pub. No. WO 2008/016988, each incorporated by reference herein).

"Separating" or "purifying" means that one or more components of a sample are removed or separated from other sample components. Sample components include target nucleic acids usually in a generally aqueous solution phase, which may also include cellular fragments, proteins, carbohydrates, lipids, and other nucleic acids. Separating or purifying removes at least 70%, or at least 80%, or at least 95% of the target nucleic acid from other sample components.

As used herein, a "DNA-dependent DNA polymerase" is an enzyme that synthesizes a complementary DNA copy from a DNA template. Examples are DNA polymerase I from *E. coli*, bacteriophage T7 DNA polymerase, or DNA polymerases from bacteriophages T4, Phi-29, M2, or T5. DNA-dependent DNA polymerases may be the naturally occurring enzymes isolated from bacteria or bacteriophages or expressed recombinantly, or may be modified or "evolved" forms which have been engineered to possess certain desirable characteristics, e.g., thermostability, or the ability to recognize or synthesize a DNA strand from various modified templates. All known DNA-dependent DNA polymerases require a complementary primer to initiate synthesis. It is known that under suitable conditions a DNA-dependent DNA polymerase may synthesize a complementary DNA copy from an RNA template. RNA-dependent DNA polymerases typically also have DNA-dependent DNA polymerase activity.

As used herein, a "DNA-dependent RNA polymerase" or "transcriptase" is an enzyme that synthesizes multiple RNA copies from a double-stranded or partially double-stranded DNA molecule having a promoter sequence that is usually double-stranded. The RNA molecules ("transcripts") are synthesized in the 5'-to-3' direction beginning at a specific position just downstream of the promoter. Examples of transcriptases are the DNA-dependent RNA polymerase from *E. coli* and bacteriophages T7, T3, and SP6.

As used herein, an "RNA-dependent DNA polymerase" or "reverse transcriptase" ("RT") is an enzyme that synthesizes a complementary DNA copy from an RNA template. All known reverse transcriptases also have the ability to make a complementary DNA copy from a DNA template; thus, they are both RNA- and DNA-dependent DNA polymerases. RTs may also have an RNAse H activity. A primer is required to initiate synthesis with both RNA and DNA templates.

As used herein, a "selective RNAse" is an enzyme that degrades the RNA portion of an RNA:DNA duplex but not single-stranded RNA, double-stranded RNA or DNA. An exemplary selective RNAse is RNAse H. Enzymes possessing the same or similar activity as RNAse H may also be used. Selective RNAses may be endonucleases or exonucleases. Most reverse transcriptase enzymes contain an RNAse H activity in addition to their polymerase activities. However, other sources of the RNAse H are available without an associated polymerase activity. The degradation may result in separation of RNA from a RNA:DNA complex. Alternatively, a selective RNAse may simply cut the RNA at various locations such that portions of the RNA melt off or permit enzymes to unwind portions of the RNA. Other enzymes that selectively degrade RNA target sequences or RNA products of the present invention will be readily apparent to those of ordinary skill in the art.

The term "specificity," in the context of an amplification and/or detection system, is used herein to refer to the characteristic of the system which describes its ability to distinguish between target and non-target sequences dependent on sequence and assay conditions. In terms of nucleic acid amplification, specificity generally refers to the ratio of the number of specific amplicons produced to the number of side-products (e.g., the signal-to-noise ratio). In terms of detection, specificity generally refers to the ratio of signal produced from target nucleic acids to signal produced from non-target nucleic acids.

The term "sensitivity" is used herein to refer to the precision with which a nucleic acid amplification reaction can be detected or quantitated. The sensitivity of an amplification reaction is generally a measure of the smallest copy number of the target nucleic acid that can be reliably detected in the amplification system, and will depend, for example, on the detection assay being employed, and the specificity of the amplification reaction, e.g., the ratio of specific amplicons to side-products.

As used herein, a "colony-forming unit" ("CFU") is used as a measure of viable microorganisms in a sample. A CFU is an individual viable cell capable of forming on a solid medium a visible colony whose individual cells are derived by cell division from one parental cell. One CFU corresponds to 1000 copies of rRNA.

As used herein, the term "relative light unit" ("RLU") is an arbitrary unit of measurement indicating the relative number of photons emitted by the sample at a given wavelength or band of wavelengths. RLU varies with the characteristics of the detection means used for the measurement.

BRIEF DESCRIPTION OF THE DRAWINGS

FIG. 1 illustrates a reference sequence for *Megasphaera elsdenii* 16S ribosomal rRNA gene (SEQ ID NO:45), partial sequence found at GenBank under accession number AY038996.1 and GI:15145820 (Oct. 15, 2002).

DETAILED DESCRIPTION OF THE INVENTION

The present invention provides compositions, kits and methods for amplifying and detecting *Megasphaera* sp. nucleic acid from a sample, specifically sequences of *Megasphaera* 16S rRNA or genes encoding 16S rRNA. Preferably, the samples are biological samples. The compositions, kits and methods provide oligonucleotide sequences that recognize target sequences of *Megasphaera* 16S rRNA or their complementary sequences, or genes encoding 16S rRNA or their complementary sequences. Such oligonucleotides may be used as amplification oligonucleotides, which may include primers, promoter primers, blocked oligonucleotides, and promoter provider oligonucleotides, whose functions have been described previously (see, e.g., U.S. Pat. Nos. 4,683,195; 4,683,202; 4,800,159; 5,399,491; 5,554,516; 5,824,518; and 7,374,885; each incorporated by reference herein). Other oligonucleotides may be used as probes for detecting amplified sequences of *Megasphaera*.

The methods provide for the sensitive and specific detection of *Megasphaera* nucleic acids. The methods include performing a nucleic acid amplification of *Megasphaera* sequences and detecting the amplified product by, for example, specifically hybridizing the amplified product with a nucleic acid detection probe that provides a signal to indicate the presence of *Megasphaera* in the sample. The amplification step includes contacting the sample with one or more amplification oligomers specific for a target sequence in 16S rRNA to produce an amplified product if *Megasphaera* nucleic acid is present in the sample. Amplification synthesizes additional copies of the target sequence or its complement by using at least one nucleic acid polymerase to extend the sequence from an amplification oligomer (a primer) using a template strand. One embodiment for detecting the amplified product uses a hybridizing step that includes contacting the amplified product with at least one probe specific for a sequence amplified by the selected amplification oligomers, e.g., a sequence contained in the target sequence flanked by a pair of selected primers.

The detection step may be performed using any of a variety of known techniques to detect a signal specifically associated with the amplified target sequence, such as, e.g., by hybridizing the amplification product with a labeled detection probe and detecting a signal resulting from the labeled probe. The detection step may also provide additional information on the amplified sequence, such as, e.g., all or a portion of its nucleic acid base sequence. Detection may be performed after the amplification reaction is completed, or may be performed simultaneously with amplifying the target region, e.g., in real time. In one embodiment, the detection step allows homogeneous detection, e.g., detection of the hybridized probe without removal of unhybridized probe from the mixture (see, e.g., U.S. Pat. Nos. 5,639,604 and 5,283,174, each incorporated by reference herein).

In embodiments that detect the amplified product near or at the end of the amplification step, a linear detection probe may be used to provide a signal to indicate hybridization of the probe to the amplified product. One example of such detection uses a luminescently labeled probe that hybridizes to target nucleic acid. Luminescent label is then hydrolyzed from non-hybridized probe. Detection is performed by chemiluminescence using a luminometer. (see, e.g., International Patent Application Pub. No. WO 89/002476, incorporated by reference herein). In other embodiments that use real-time detection, the detection probe may be a hairpin probe such as, for example, a molecular beacon, molecular torch, or hybridization switch probe that is labeled with a reporter moiety that is detected when the probe binds to amplified product. Such probes may comprise target-hybridizing sequences and non-target-hybridizing sequences. Various forms of such probes have been described previously (see, e.g., U.S. Pat. Nos. 5,118,801; 5,312,728; 5,925,517; 6,150,097; 6,849,412; 6,835,542; 6,534,274; and 6,361,945; and US Patent Application Pub. Nos. 20060068417A1 and 20060194240A1; each incorporated by reference herein).

A reference sequence for *Megasphaera elsdenii* 16S ribosomal rRNA gene (SEQ ID NO:45) is shown in FIG. 1. This sequence, from a bovine strain of *M. elsdenii*, YJ-4, shows a high degree of sequence identity to 16S rRNA sequences from other bovine *M. elsdenii* strains (see, e.g., Kim et al., *J. App. Microbiol.* 92:976-982, 2002), and available GenBank sequences from bovine strains of *M. elsdenii* have been shown to be closely related to *Megasphaera*-like species associated with bacterial vaginosis in human (see, e.g., Fredricks et al., *N. Eng. J. Med.* 353:1899-1911, 2005). Thus, the 16S rRNA sequence of SEQ ID NO:45 is a particularly suitable reference sequence when describing certain aspects of the present invention herein.

Preferred compositions of the instant invention are configured to specifically hybridize to a 16S rRNA nucleic acid of *Megasphaera* sp. with minimal cross-reactivity to other nucleic acids suspected of being in a sample. In some aspects, the compositions of the instant invention are configured to specifically hybridize to a 16S rRNA nucleic acid of *Megasphaera* sp. with minimal cross-reactivity to one or more of anaerobic gram-positive cocci; *A. vaginae*; *Lactobacillus* sp.; *Lactobacillus iners*; *Lactobacillus crispatus* group; *Lactobacillus gasseri* group; *Gardnerella* sp.; *Gardnerella vaginalis*; *Trichomonas* sp.; *Trichomonas vaginalis*; *Candida* sp.; *Eggerthella* sp.; Bacterium from the order Clostridiales; *Clostridium*-like sp.; *Prevotella* sp.; *Prevotella bivia* group; *Prevotella buccalis* group; *Atopobium* sp.; *Atopobium vaginae*; Enterobacteria; *Peptostreptococcus micros*; *Aerococcus christensenii*; *Leptotrichia amnionii*; *Peptoniphilus* sp.; *Dialister* sp.; *Mycoplasma hominis*; *Sneathia sanguinegens*; *Anaerococcus tetradius*; *Mobiluncus* sp.; *Mobiluncus hominis*; *Eggerthella hongkongensis*; *Leptotrichia sanguinegens* and *Finegoldia magna*. In one aspect, the compositions of the instant invention are part of a multiplex system that further includes components and methods for detecting one of more of these organisms.

In certain aspects of the invention, a combination of at least two oligomers is provided for the detection of a *Megasphaera* sp. 16S rRNA or a gene encoding a *Megasphaera* sp. 16S rRNA. For example, in some embodiments the oligomer combination is for amplification of a *Megasphaera* target region substantially corresponding to SEQ ID NO:45 from about nucleotide position 290 to about nucleotide position 334. Particularly suitable oligomers for the oligomer combination include (1) a first amplification oligomer comprising a target-hybridizing sequence that is from about 15 to about 25 contiguous nucleotides in length and substantially corresponding to, or identical to, a sequence that is contained in the sequence of SEQ ID NO:34 (5'-AGTTGGAGGGGTA ACGGCCCAACAAGGCGAT-GATCAG-3') and includes at least the sequence of SEQ ID NO:28 (5'-GCCCAACAAGGCGA-3'); and (2) a second amplification oligomer comprising a target-hybridizing sequence that is from about 15 to about 25 contiguous nucleotides in length and substantially corresponding to, or identical to, a sequence that is contained in the sequence of SEQ ID NO:36 (5'-CCTCCCGTAGGAGTNTGGGCCGT-GTCTCAGTCCC-3') and includes at least the sequence of SEQ ID NO:35 (5'-GAGTNTGGGCCGTG-3'). In some such embodiments, the target-hybridizing sequence of the first amplification oligomer substantially corresponds to, or is identical to, a sequence that is contained in the sequence of SEQ ID NO:29 (5'-GTNACGGCCCARCAAGGCG-AK-GATCAG-3'); and/or the target-hybridizing sequence of the second amplification oligomer substantially corresponds to, or is identical to, a sequence that is contained in the sequence of SEQ ID NO:33 (5'-CGTAGGAGTNTGGGCCGT-GTCTCAG-3'). In other embodiments of an oligomer combination as above, the target-hybridizing sequence of the second amplification oligomer substantially corresponds to, or is identical to, a sequence that includes at least the sequence of SEQ ID NO:32 (5'-GTAGGAGTNTGGGC-CGTGTCTC-3'). In specific variations, the target-hybridizing sequence of the first amplification oligomer consists of a sequence substantially corresponding to, or identical to, the sequence shown in SEQ ID NO:13 (5'-GTAACGGC-CCAACAAGGCGA-3') or SEQ ID NO:14 (5'-GC-CCAACAAGGCGATGATCAG-3'); and/or the target-hybridizing sequence of the second amplification oligomer consists of a sequence substantially corresponding to, or identical to, the sequence shown in SEQ ID NO:19 (5'-GTAGGAGTCTGGGCCGTGTCTCAG-3') or SEQ ID NO:20 (5'-CGTAGGAGTCTGGGCCGTGTCTC-3').

In other embodiments, the oligomer combination is for amplification of a *Megasphaera* target region substantially corresponding to SEQ ID NO:45 from about nucleotide position 466 to about nucleotide position 607. Particularly suitable oligomers for the oligomer combination include (1) a first amplification oligomer comprising a target-hybridizing sequence that is from about 15 to about 25 contiguous nucleotides in length and substantially corresponding to, or identical to, a sequence that is contained in the sequence of SEQ ID NO:38 (5'-GGTTGTAAAGTTC TGT-TATACGGGACGAATGG-3') and includes at least the sequence of SEQ ID NO:37 (5'-CTGTT ATACGGGAC-3'); and (2) a second amplification oligomer comprising a target-hybridizing sequence that is from about 15 to about 25 contiguous nucleotides in length and substantially corresponding to, or identical to, a sequence that is contained in the sequence of SEQ ID NO:40 (5'-GCCCCGCACTTT-TAAGACCGACTTACGACGC-3') and includes at least the sequence of SEQ ID NO:39 (5'-CTTTTAAGACCGAC-3'). In specific variations, the target-hybridizing sequence of the first amplification oligomer consists of a sequence substantially corresponding to, or identical to, the sequence shown in SEQ ID NO:15 (5'-CTGTTATACGGGACGAAT-3'); and/or the target-hybridizing sequence of the second amplification oligomer consists of a sequence substantially corresponding to, or identical to, the sequence shown in SEQ ID NO:21 (5'-CCGCACTTTTAAGAC CGACTTA-3').

In certain embodiments, an amplification oligomer as described herein is a promoter primer further comprising a promoter sequence located 5' to the target-hybridizing sequence and which is non-complementary to the *Megasphaera* target nucleic acid. For example, in some embodiments of an oligomer combination as described herein for amplification of a *Megasphaera* target region substantially corresponding to SEQ ID NO:45 from about nucleotide position 290 to about nucleotide position 334 or from about nucleotide position 466 to about nucleotide position 607, the second amplification oligomer is a promoter primer further comprising a 5' promoter sequence. In particular embodiments, the promoter sequence is a T7 RNA polymerase promoter sequence such as, for example, a T7 promoter sequence having the sequence shown in SEQ ID NO:22 (5'-AATTTAATACGACTCACTATAGGGAGA-3'). In specification variations of an oligomer combination as described herein for amplification of a *Megasphaera* target region substantially corresponding to SEQ ID NO:45 from about nucleotide position 290 to about nucleotide position 334, the second amplification oligomer is a promoter primer having the sequence shown in SEQ ID NO:16 (5'-AATT-TAATACGACTCACTATAGGGAGAGTAGGAGTCTGG GCCGTGTCTCAG-3') or SEQ ID NO:17 (5'-AATT-TAATACGACTCACTATAGGGAGACGTAG-GAGTCTGGGCCGTGTC TC-3'). In specific variations of an oligomer combination as described herein for amplification of a *Megasphaera* target region substantially corresponding to SEQ ID NO:45 from about nucleotide position 466 to about nucleotide position 607, the second amplification oligomer is a promoter primer having the sequence shown in SEQ ID NO:18 (5'-AATTTAATACGACTCAC-TATAGGGAGACCG CACTTTTAAGACCGACTTA-3').

In some embodiments, an oligomer combination as described herein further comprises at least one capture probe oligomer comprising a target-hybridizing sequence substantially corresponding to a sequence contained in the complement of SEQ ID NO:45, wherein the target-hybridizing sequence is covalently attached to a sequence or moiety that binds to an immobilized probe. In specific variations, the target-hybridizing sequence comprises or consists of a sequence substantially corresponding to, or identical to, a sequence selected from SEQ ID NO:7 (5'-CTACTGC TGC-CTCCCGTAGGAG-3'), SEQ ID NO:8 (5'-GGACTACCA-GGGTATCTAATCCTG-3'), SEQ ID NO:9 (5'-CGACAC-GAGCTGACGACAGCCATGCA-3'), SEQ ID NO:10 (5'-GACGTCATCCC CACCTTCCT-3'), SEQ ID NO:11 (5'-CGTATTCGGTATTAGCAGCCG-3'), and SEQ ID NO:12 (5'-GCTGGCACGTAGTTAGCCGTGGCT-3'). Particularly suitable capture probes for use in accordance with the present invention comprise or consist of a sequence selected from SEQ ID NO:1 (5'-CTACTGCTGCCTCCCGTAG-GAGTTTAAAAAAAAAAAAAAAAAA-3'), SEQ ID NO:2 (5'-GGACTACCAGGGTATCTAATCCTGTT-TAAAAAAAAAAAAAAAAAAA AAAAAAAAAAA-3'), SEQ ID NO:3 (5'-CGACACGAGCTGACGACAGCCATG-CATTTAAAAAAAAAAAAAAAAAAAAAAAAAAA AAA-3'), SEQ ID NO:4 (5'-GACGTCATCCCCACCT-TCCT TTTAAAAAAAAAAAAAAAAAAAAAAAA AAAAAA-3'), SEQ ID NO:5 (5'-CGTATTCGGTAT TAGCAGCCGTTTAAAAAAAAAAAAAAAAAAAAA AAAAAAAA-3'), and SEQ ID NO:6 (5'-GCTGGCACG-TAGTTAGCCGTGGCTTTTAAAAAAAAAAAAAAAA AAAAAAAAAAAAAAA-3').

In certain variations, an oligomer combination as described herein further comprises at least one detection probe oligomer configured to specifically hybridize to a *Megasphaera* target sequence that is amplifiable using the first and second amplification oligomers (e.g., a *Megasphaera* target sequence that is flanked by the target-hybridizing sequences of the first and second amplification oligomers). In some embodiments, a detection probe oligomer for use in accordance with the present invention comprises a target-hybridizing sequence that is from about 14 to about 40 nucleotides in length and is configured to specifically hybridize to a target sequence contained within a *Megasphaera* target region from about nucleotide position 290 to about nucleotide position 334 of SEQ ID NO:45. For example, in some variations, the detection probe oligomer comprises a target-hybridizing sequence substantially corresponding to, or identical to, a sequence that is contained in the sequence of SEQ ID NO:31 (5'-CAGTAGCCGGTCT-GAGAGGATGAACG-3') and includes at least the sequence of SEQ ID NO:30 (5'-GTAGCCGGTCTGAGAGGATGA-3'). Particularly suitable detection probe oligomers include, for example, oligomers comprising a target-hybridizing sequence substantially corresponding to, or identical to, a sequence selected from SEQ ID NO:23 (5'-CAGTAGCCG-GTCTGAGAGGATGA-3') and SEQ ID NO:25 (5'-GTAGCCGGTCTGAGAGGAT GAACG-3').

In other embodiments, a detection probe oligomer for use in accordance with the present invention comprises a target-hybridizing sequence that is from about 14 to about 40 nucleotides in length and is configured to specifically hybridize to a target sequence contained within a *Megasphaera* target region from about nucleotide position 466 to about nucleotide position 607 of SEQ ID NO:45, or to a target sequence contained within a *Megasphaera* target region from about nucleotide position 466 to about nucleotide position 536 of SEQ ID NO:45. For example, in some variations, the detection probe oligomer comprises a target-hybridizing sequence substantially corresponding to, or identical to, a sequence that is contained in the sequence of SEQ ID NO:24 (5'-GACGGTACCGTAAGAGAAAGCC-3') and includes at least the sequence of SEQ ID NO:26 (5'-CGGTACCGTAAGAGAAAG-3'). Particularly suitable detection probe oligomers include, for example, oligomers comprising a target-hybridizing sequence substantially corresponding to, or identical to, a sequence selected from SEQ ID NO:24 and SEQ ID NO:26.

Typically, a detection probe oligomer in accordance with the present invention further includes a label. Particularly suitable labels include compounds that emit a detectable light signal, e.g., fluorophores or luminescent (e.g., chemiluminescent) compounds that can be detected in a homogeneous mixture. More than one label, and more than one type of label, may be present on a particular probe, or detection may rely on using a mixture of probes in which each probe is labeled with a compound that produces a detectable signal (see, e.g., U.S. Pat. Nos. 6,180,340 and 6,350,579, each incorporated by reference herein). Labels may be attached to a probe by various means including covalent linkages, chelation, and ionic interactions, but preferably the label is covalently attached. For example, in some embodiments, a detection probe has an attached chemiluminescent label such as, e.g., an acridinium ester (AE) compound (see, e.g., U.S. Pat. Nos. 5,185,439; 5,639,604; 5,585,481; and 5,656,744; each incorporated by reference herein), which in typical variations is attached to the probe by a non-nucleotide linker (see, e.g., U.S. Pat. Nos. 5,585,481; 5,656,744; and 5,639,604, particularly at column 10, line 6 to column 11, line 3, and Example 8; each incorporated by reference herein). In other embodiments, a detection probe comprises both a fluorescent label and a quencher, a combination that is particularly useful in fluorescence resonance energy transfer (FRET) assays. Specific variations of such detection probes include, e.g., a TaqMan detection probe (Roche Molecular Diagnostics) and a "molecular beacon" (see, e.g., Tyagi et al., *Nature Biotechnol.* 16:49-53, 1998; U.S. Pat. Nos. 5,118,801 and 5,312,728; each incorporated by reference herein).

A detection probe oligomer in accordance with the present invention may further include a non-target-hybridizing sequence. Specific embodiments of such detection probes include, for example, probes that form conformations held by intramolecular hybridization, such as conformations generally referred to as hairpins. Particularly suitable hairpin probes include a "molecular torch" (see, e.g., U.S. Pat. Nos. 6,849,412; 6,835,542; 6,534,274; and 6,361,945, each incorporated by reference herein) and a "molecular beacon" (see, e.g., Tyagi et al., supra; U.S. Pat. No. 5,118,801 and U.S. Pat. No. 5,312,728, supra). Methods for using such hairpin probes are well known in the art.

In yet other embodiments, a detection probe is a linear oligomers that does not substantially form conformations held by intramolecular bonds. In specific variations, a linear detection probe oligomer includes a chemiluminescent compound as the label, preferably an AE compound.

In yet other variations, an oligomer combination for detection of a *Megasphaera* nucleic acid further comprises a pseudotarget oligomer that can be amplified using first and second amplification oligomers as described herein. Typically, the pseudotarget oligomer is sufficiently distinct from the target region of *Megasphaera* nucleic acid flanked by the amplification oligomers, such that a detection probe configured to specifically hybridize to a *Megasphaera*-specific amplification product, generated using the amplification oligomers on a *Megasphaera* target nucleic acid template, will not specifically hybridize to an amplification product generated using the same amplification oligomers with the pseudotarget oligomer template. Pseudotargets may be used to adjust assay sensitivity by changing the cutoff used to classify a sample as positive or negative, rather than re-optimizing the entire amp system to get lower sensitivity through lower amplification efficiency. Accordingly, such pseudotarget oligomers are particularly useful for "detuning" assay sensitivity in certain embodiments of the detection methods described herein. In a specific embodiment, the pseudotarget oligomer has a sequence substantially corresponding to, or identical to, a sequence selected from SEQ ID NO:27 (5'-CTGTTATACGGGACGAATTAAGTCG-GTCTTAAAAGTGCGG-3') (amplifiable using, e.g., amplification oligomers comprising target-hybridizing sequences of SEQ ID NOs:15 and 18); SEQ ID NO:41 (5'-GTAACG-GCCCAACAAGGCGACTGA GACACGGCCCA-GACTCCTAC-3') (amplifiable using, e.g., amplification oligomers comprising target-hybridizing sequences of SEQ ID NOs:13 and 19); SEQ ID NO:42 (5'-GTAACGGC-CCAACA AGGCGAGAGACACGGCCCAGACTC-CTACG-3') (amplifiable using, e.g., amplification oligomers comprising target-hybridizing sequences of SEQ ID NOs:13 and 20); SEQ ID NO:43 (5'-GCCCAACAAGGCGAT-GATCAGCTGAGACACGGCCCAGACTCCTAC-3') (amplifiable using, e.g., amplification oligomers comprising target-hybridizing sequences of SEQ ID NOs:14 and 19); and SEQ ID NO:44 (5'-GCCCAACAAGGCGATGATCA-GGAGACACGGCCCAGACTCCTACG-3') (amplifiable using, e.g., amplification oligomers comprising target-hybridizing sequences of SEQ ID NOs:14 and 20).

Also provided by the present invention are detection probe oligomers, capture probe oligomers, and pseudotarget oligomers as described herein.

In another aspect, the present invention provides methods for detecting a *Megasphaera* sp. 16S rRNA or a gene encoding a *Megasphaera* sp. 16S rRNA in a sample using a combination of at least two oligomers as described herein. Such a method generally includes (a) providing a sample suspected of containing a *Megasphaera* sp. bacterium; (b) contacting the sample with at least two oligomers for amplifying a *Megasphaera* sp. nucleic acid target region corresponding to a *Megasphaera* 16S rRNA target nucleic acid, where the oligomer combination includes first and second amplification oligomers as described above for either a first or second target region; (c) performing an in vitro nucleic acid amplification reaction, where any *Megasphaera* target nucleic acid present in the sample is used as a template for generating an amplification product; and (d) detecting the presence or absence of the amplification product, thereby indicating the presence or absence of *Megasphaera* sp. in the sample.

In certain embodiments, the method further includes purifying the *Megasphaera* target nucleic acid from other components in the sample before the amplification step. Such purification may include may include methods of separating and/or concentrating organisms contained in a sample from other sample components. In particular embodiments, purifying the target nucleic acid includes capturing the target nucleic acid to specifically or non-specifically separate the target nucleic acid from other sample components. Non-specific target capture methods may involve selective precipitation of nucleic acids from a substantially aqueous mixture, adherence of nucleic acids to a support that is washed to remove other sample components, or other means of physically separating nucleic acids from a mixture that contains *Megasphaera* nucleic acid and other sample components.

In some embodiments, a 16S rRNA target nucleic of *Megasphaera* sp. or a gene encoding the 16S rRNA of *Megasphaera* is selectively separated from other sample components by specifically hybridizing the *Megasphaera* target nucleic acid to a capture probe oligomer. The capture probe oligomer comprises a target-hybridizing sequence configured to specifically hybridize to a *Megasphaera* 16S rRNA target sequence so as to form a target-sequence:capture-probe complex that is separated from sample components. Suitable capture probe target-hybridizing sequences include, e.g., the sequences shown in SEQ ID NOs:7-12. In a preferred variation, the specific target capture binds the *Megasphaera* 16S rRNA target:capture-probe complex to an immobilized probe to form a target:capture-probeimmobilized-probe complex that is separated from the sample and, optionally, washed to remove non-target sample components (see, e.g., U.S. Pat. Nos. 6,110,678; 6,280,952; and 6,534,273; each incorporated by reference herein). In such variations, the capture probe oligomer further comprises a sequence or moiety that binds attaches the capture probe, with its bound target sequence, to an immobilized probe attached to a solid support, thereby permitting the hybridized target nucleic acid to be separated from other sample components.

In more specific embodiments, the capture probe oligomer includes a tail portion (e.g., a 3' tail) that is not complementary to the *Megasphaera* sp. 16S rRNA target sequence but that specifically hybridizes to a sequence on the immobilized probe, thereby serving as the moiety allowing the target nucleic acid to be separated from other sample components, such as previously described in, e.g., U.S. Pat. No. 6,110,678, incorporated herein by reference. Any sequence may be used in a tail region, which is generally about 5 to 50 nt long, and preferred embodiments include a substantially homopolymeric tail of about 10 to 40 nt (e.g., $A_{10}$ to $A_{40}$), more preferably about 14 to 33 nt (e.g., $A_{14}$ to $A_{30}$ or $T_3A_{14}$ to $T_3A_{30}$), that bind to a complementary immobilized sequence (e.g., poly-T) attached to a solid support, e.g., a matrix or particle. For example, in specific embodiments of a capture probe comprising a 3' tail, the capture probe has a sequence selected from SEQ ID NOs: 1-6.

Target capture typically occurs in a solution phase mixture that contains one or more capture probe oligomers that hybridize specifically to the 16S rRNA of *Megasphaera* sp. or gene target sequence under hybridizing conditions, usually at a temperature higher than the $T_m$ of the tail-sequence:immobilized-probe-sequence duplex. For embodiments comprising a capture probe tail, the *Megasphaera*-16S-rRNA-target:capture-probe complex is captured by adjusting the hybridization conditions so that the capture probe tail hybridizes to the immobilized probe, and the entire complex on the solid support is then separated from other sample components. The support with the attached immobilized-probe:capture-probe:*Megasphaera*-16S-rRNA-target-sequence may be washed one or more times to further remove other sample components. Preferred embodiments use a particulate solid support, such as paramagnetic beads, so that particles with the attached *Megasphaera*-16S-rRNA-target:capture-probeimmobilized-probe complex may be suspended in a washing solution and retrieved from the washing solution, preferably by using magnetic attraction. To limit the number of handling steps, the *Megasphaera* sp. 16S rRNA target nucleic acid may be amplified by simply mixing the *Megasphaera* 16S rRNA target sequence in the complex on the support with amplification oligomers and proceeding with amplification steps.

Amplifying a *Megasphaera* target sequence utilizes an in vitro amplification reaction using at least two amplification oligomers that flank a target region to be amplified. In particular embodiments, the target region to be amplified substantially corresponds to SEQ ID NO:45 from about nucleotide position 290 about nucleotide position 334, or from about nucleotide position 466 to about 607. Particularly suitable amplification oligomer combinations for amplification of these target regions are described herein. Suitable amplification methods include, for example, replicase-mediated amplification, polymerase chain reaction (PCR), ligase chain reaction (LCR), strand-displacement amplification (SDA), and transcription-mediated or transcription-associated amplification (TMA). Such amplification methods are well-known in the art and are readily used in accordance with the methods of the present invention.

For example, amplification methods that use TMA amplification include the following steps. Briefly, the target nucleic acid that contains the sequence to be amplified is provided as single stranded nucleic acid (e.g., ssRNA or ssDNA). Those skilled in the art will appreciate that conventional melting of double stranded nucleic acid (e.g., dsDNA) may be used to provide single-stranded target nucleic acids. A promoter primer binds specifically to the target nucleic acid at its target sequence and a reverse transcriptase (RT) extends the 3' end of the promoter primer using the target strand as a template to create a cDNA copy of the target sequence strand, resulting in an RNA:DNA duplex. An RNase digests the RNA strand of the RNA:DNA duplex and a second primer binds specifically to its target sequence, which is located on the cDNA strand downstream from the promoter primer end. RT synthesizes a new DNA strand by extending the 3' end of the second primer using the first cDNA template to create a dsDNA that contains a functional promoter sequence. An RNA polymerase specific for the promoter sequence then initiates transcription to produce RNA transcripts that are about 100 to 1000 amplified copies ("amplicons") of the initial target strand in the reaction. Amplification continues when the second primer binds specifically to its target sequence in each of the amplicons and RT creates a DNA copy from the amplicon RNA template to produce an RNA:DNA duplex. RNase in the reaction mixture digests the amplicon RNA from the RNA:DNA duplex and the promoter primer binds specifically to its complementary sequence in the newly synthesized DNA. RT extends the 3' end of the promoter primer to create a dsDNA that contains a functional promoter to which the RNA polymerase binds to transcribe additional amplicons that are complementary to the target strand. The autocatalytic cycles of making more amplicon copies repeat during the course of the reaction resulting in about a billion-fold amplification of the target nucleic acid present in the sample. The amplified products may be detected in real-time during amplification, or at the end of the amplification reaction by using a probe that binds specifically to a target sequence contained in the amplified products. Detection of a signal resulting from the bound probes indicates the presence of the target nucleic acid in the sample.

Detection of the amplified products may be accomplished by a variety of methods. The nucleic acids may be associated with a surface that results in a physical change, such as a detectable electrical change. Amplified nucleic acids may be detected by concentrating them in or on a matrix and detecting the nucleic acids or dyes associated with them (e.g., an intercalating agent such as ethidium bromide or cyber green), or detecting an increase in dye associated with nucleic acid in solution phase. Other methods of detection may use nucleic acid detection probes that are configured to specifically hybridize to a sequence in the amplified product and detecting the presence of the probe:product complex, or by using a complex of probes that may amplify the detectable signal associated with the amplified products (e.g., U.S. Pat. Nos. 5,424,413; 5,451,503; and 5,849,481; each incorporated by reference herein). Directly or indirectly labeled probes that specifically associate with the amplified product provide a detectable signal that indicates the presence of the target nucleic acid in the sample. For example, if the target nucleic acid is the 16S rRNA of *Megasphaera* sp., the amplified product will contain a target sequence in or complementary to a sequence in the 16S rRNA of *Megasphaera*, and a probe will bind directly or indirectly to a sequence contained in the amplified product to indicate the presence of the 16S rRNA of *Megasphaera* in the tested sample.

Preferred embodiments of detection probes that hybridize to the complementary amplified sequences may be DNA or RNA oligomers, or oligomers that contain a combination of DNA and RNA nucleotides, or oligomers synthesized with a modified backbone, e.g., an oligomer that includes one or more 2'-methoxy substituted ribonucleotides. Probes used for detection of the amplified *Megasphaera* sp. rRNA sequences may be unlabeled and detected indirectly (e.g., by binding of another binding partner to a moiety on the probe) or may be labeled with a variety of detectable labels. Particular embodiments of detection probes suitable for use in accordance with methods of the present invention are further described herein.

Oligomers that are not intended to be extended by a nucleic acid polymerase preferably include a blocker group that replaces the 3' OH to prevent enzyme-mediated extension of the oligomer in an amplification reaction. For example, blocked amplification oligomers and/or detection probes present during amplification preferably do not have a functional 3' OH and instead include one or more blocking groups located at or near the 3' end. A blocking group near the 3' end is preferably within five residues of the 3' end and is sufficiently large to limit binding of a polymerase to the oligomer, and other preferred embodiments contain a blocking group covalently attached to the 3' terminus. Many different chemical groups may be used to block the 3' end, e.g., alkyl groups, non-nucleotide linkers, alkane-diol dideoxynucleotide residues, and cordycepin. A preferred method for detecting *Megasphaera* sp. 16S rRNA sequences uses a transcription-associated amplification with a linear chemiluminescently labeled probe, more preferably, a linear AE labeled probe.

Assays for detection of the *Megasphaera* sp. 16S rRNA nucleic acid may optionally include a non-*Megasphaera* sp. 16S rRNA internal control (IC) nucleic acid that is amplified and detected in the same assay reaction mixtures by using amplification and detection oligomers specific for the IC sequence. IC nucleic acid sequences can be synthetic nucleic acid sequences that are spiked into a sample or the IC nucleic acid sequences may be cellular component. IC nucleic acid sequences that are cellular components can be from exogenous cellular sources or endogenous cellular sources relative to the specimen. An exogenous cellular source, for example, is a cell that is added into the sample and that then flows through the sample processing procedures along with the specimen. A more particular example would be the addition of a HeLa cell, Jurkat cell, SiLa cell or other to the sample medium along with the specimen that is collected for testing (e.g., a vaginal swab specimen). The specimen and the exogenous cells are then processed, amplified and detected. The specimen being amplified and detected using amplification and detection oligomers for identifying the target sequence of interest and the exogenous cells being amplified and detected using amplification and detection oligomers for identifying an IC target sequence such as 18S rRNA. An endogenous cellular source is a cellular source that would naturally be obtained when gathering the specimen. One example: epithelial cells will present when obtaining a specimen via a vaginal swab. Similar then to the above exemplary exogenous cells process described, the specimen and the endogenous cellular source are both processed, amplified, and detected. The specimen being amplified and detected using amplification and detection oligomers for identifying the target sequence of interest and the endogenous cells being amplified and detected using amplification and detection oligomers for identifying an IC target sequence; typically a housekeeping gene present in the endogenous cellular source, such as a beta-globulin gene. (See e.g., Poljak et al., J. Clin. Virol, 25: S89-97, 2002; U.S. Pat. No. 6,410,321; and US Patent Application Publication No. 2004-0023288; each incorporated by reference herein). Use of a cellular source IC allows for a control from sample collection through detection. Synthetic nucleic acid sequences provide for control of amplification and detection.

In certain embodiments, amplification and detection of a signal from the amplified IC sequence demonstrates that the assay reagents, conditions, and performance of assay steps were properly used in the assay if no signal is obtained for the intended target *Megasphaera* sp. nucleic acid (e.g., samples that test negative for the 16S rRNA of *Megasphaera* sp.). An IC may also be used as an internal calibrator for the assay when a quantitative result is desired, i.e., the signal obtained from the IC amplification and detection is used to set a parameter used in an algorithm for quantitating the amount of *Megasphaera* nucleic acid in a sample based on the signal obtained for amplified an *Megasphaera* 16S rRNA target sequence. ICs are also useful for monitoring the integrity of one or more steps in an assay. A preferred embodiment of a synthetic IC nucleic acid sequence is a randomized sequence that has been derived from a naturally occurring source (e.g., an HW sequence that has been rearranged in a random manner). Another preferred IC nucleic acid sequence may be an RNA transcript isolated from a naturally occurring source or synthesized in vitro, such as by making transcripts from a cloned randomized sequence such that the number of copies of IC included in an assay may be accurately determined. The primers and probe for the IC target sequence are configured and synthesized by using any well-known method provided that the primers and probe function for amplification of the IC target sequence and detection of the amplified IC sequence using substantially the same assay conditions used to amplify and detect the *Megasphaera* target sequence. In preferred embodiments that include a target capture-based purification step, it is preferred that a target capture probe specific for the IC target be included in the assay in the target capture step so that the IC is treated in the assay in a manner analogous to that for the intended *Megasphaera* analyte in all of the assay steps.

Assays for detection of the *Megasphaera* sp. 16S rRNA nucleic acid may optionally include a pseudotarget. A "pseudotarget" is an oligonucleotide that can be co-amplified with the target polynucleotide in a single amplification reaction. The pseudotarget and target polynucleotide may be amplified using the same set of oligonucleotide primers. The pseudotarget and the target polynucleotide will be non-identical molecules so that the target probe will not detect the pseudotarget.

Amplification methods using pseudotargets are useful for quantifying target polynucleotides present in a test sample. These methods includes steps for: (1) obtaining a test sample that contains an unknown amount of an target polynucleotide; (2) combining a predetermined amount of this test sample with a predetermined amount of a pseudotarget; (3) co-amplifying in an amplification reaction the target polynucleotide and the pseudotarget to produce a collection of amplification products that includes both a target amplicon and a pseudotarget amplicon; and (4) quantifying the target amplicon without relying on information regarding the amount of pseudotarget amplicon produced in the reaction, whereby the quantity of target amplicon is related in a dose-dependent manner to the unknown amount target polynucleotide that was present in the original test sample. Amplification reactions that include a pseudotarget have been shown under certain conditions to provide uniform results having less variability than similar amplification reactions lacking pseudotarget. This is particularly true for amplification of samples containing a low level of target nucleic acid. Using a pseudotarget in an amplification reaction changes the probe RLU output from an all-or-none response to a response wherein the RLU output is proportional to target input. Thus, pseudotarget allows for adjustments in assay sensitivity by changing the cutoff used to classify a sample as positive or negative, rather than re-optimizing the entire amp system to get lower sensitivity through lower amplification efficiency. Pseudotargets are further advantageous for detecting low-levels of target nucleic acid in a specimen. (See also U.S. Pat. No. 6,294, 338, incorporated by reference herein).

Detecting *Megasphaera* sp. to diagnosis bacterial vaginosis in a clinical sample will preferably use higher RLU cut-off values than those used for detecting the presence/absence of *A. vaginae* from a sample. This is because for diagnosis of BV, normal samples can be positive for relatively low amounts of *Megasphaera* sp. while BV samples will have relatively greater amounts of *Megasphaera* sp. So for diagnosis, a higher RLU cut-off value is one approach to differentiating normal levels of *Megasphaera* from elevated levels present in a sample. Depending on the desired application for the amplification and detection oligomers described herein, a skilled artisan will set an appropriate RLU cut-off value, with lower values being useful for detecting all *Megasphaera* sp. present in a sample, and higher RLU values being useful for detecting a threshold amount of *Megasphaera* sp. in a sample.

Additional microbe detection assays can be similarly performed for determining the presence and/or relative amount of a plurality of microbes implicated in BV. By way of example only, such plurality of microbes can include one or more of anerobic gram-positive cocci; *Atopobium vaginae; Lactobacillus* sp.; *Lactobacillus iners; Lactobacillus crispatus* group; *Lactobacillus gasseri* group; *Gardnerella* sp.; *Gardnerella vaginalis; Trichomonas* sp.; *Trichomonas vaginalis; Candida* sp.; *Eggerthella* sp.; Bacterium from the order Clostridiales; *Clostridium*-like sp.; *Prevotella* sp.; *Prevotella bivia* group; *Prevotella buccalis* group; *Atopobium* sp.; *Atopobium vaginae*; Enterobacteria; *Peptostreptococcus micros; Aerococcus christensenii; Leptotrichia amnionii; Peptoniphilus* sp.; *Dialister* sp.; *Mycoplasma hominis; Sneathia sanguinegens; Anaerococcus tetradius; Mobiluncus* sp.; *Mobiluncus hominis; Eggerthella hongkongensis; Leptotrichia sanguinegens* and *Finegoldia magna*. Assays may be performed separately or multiplexed. Thus, a diagnosis of BV can include identifying a plurality of microbes and optionally determining their relative abundances in a sample.

Also provided by the subject invention is a reaction mixture for amplification and/or detection of a *Megasphaera* sp. target nucleic acid. A reaction mixture in accordance with the present invention at least comprises one or more of the following: an oligomer combination as described herein for amplification of a *Megasphaera* target nucleic acid; a capture probe oligomer as described herein for purifying the *Megasphaera* target nucleic acid; a detection probe oligomer as described herein for determining the presence or absence of a *Megasphaera* amplification product; and a pseudotarget oligomer as described herein for detuning sensitivity of an assay for detecting the *Megasphaera* target nucleic acid. The reaction mixture may further include a number of optional components such as, for example, arrays of capture probe nucleic acids. For an amplification reaction mixture, the reaction mixture will typically include other reagents suitable for performing in vitro amplification such as, e.g., buffers, salt solutions, appropriate nucleotide triphosphates (e.g., dATP, dCTP, dGTP, dTTP, ATP, CTP, GTP and UTP), and/or enzymes (e.g., reverse transcriptase, and/or RNA polymerase), and will typically include test sample components, in which a *Megasphaera* target nucleic acid may or may not be present. In addition, for a reaction mixture that includes a detection probe together with an amplification oligomer combination, selection of amplification oligomers and detection probe oligomers for a reaction mixture are linked by a common target region (i.e., the reaction mixture will include a probe that binds to a sequence amplifiable by an amplification oligomer combination of the reaction mixture).

Also provided by the subject invention are kits for practicing the methods as described herein. A kit in accordance with the present invention at least comprises one or more of the following: an amplification oligomer combination as described herein for amplification of a *Megasphaera* target nucleic acid; a capture probe oligomer as described herein for purifying the *Megasphaera* target nucleic acid; a detection probe oligomer as described herein for determining the presence or absence of a *Megasphaera* amplification product; and a pseudotarget oligomer as described herein for detuning sensitivity of an assay for detecting the *Megasphaera* target nucleic acid. The kits may further include a number of optional components such as, for example, arrays of capture probe nucleic acids. Other reagents that may be present in the kits include reagents suitable for performing in vitro amplification such as, e.g., buffers, salt solutions, appropriate nucleotide triphosphates (e.g., dATP, dCTP, dGTP, dTTP, ATP, CTP, GTP and UTP), and/or enzymes (e.g., reverse transcriptase, and/or RNA polymerase). Oligomers as described herein may be packaged in a variety of different embodiments, and those skilled in the art will appreciate that the invention embraces many different kit configurations. For example, a kit may include amplification oligomers for only one target region of a *Megasphaera* sp. genome, or it may include amplification oligomers for multiple *Megasphaera* sp. target regions. In addition, for a kit that includes a detection probe together with an amplification oligomer combination, selection of amplification oligomers and detection probe oligomers for a kit are linked by a common target region (i.e., the kit will include a probe that binds to a sequence amplifiable by an amplification oligomer combination of the kit). In certain embodiments, the kit further includes a set of instructions for practicing methods in accordance with the present invention, where the instructions may be associated with a package insert and/or the packaging of the kit or the components thereof.

The invention is further illustrated by the following non-limiting examples.

Example 1

Reagents

Various reagents are identified in the examples below. The formulations and pH values (where relevant) of these reagents were as follows.

A "Lysis Buffer" contains 15 mM sodium phosphate monobasic monohydrate, 15 mM sodium phosphate dibasic anhydrous, 1.0 mM EDTA disodium dihydrate, 1.0 mM EGTA free acid, and 110 mM lithium lauryl sulfate, pH 6.7.

A "Urine Lysis Buffer" contains 150 mM HEPES free acid, 294 mM lithium lauryl sulfate, 57 mM lithium hydroxide monohydrate, 100 mM ammonium sulfate, pH 7.5.

A "Target Capture Reagent" contains 250 mM HEPES free acid dihydrate, 310 mM lithium hydroxide monohydrate, 1.88 M lithium chloride, 100 mM EDTA free acid, 2 M lithium hydroxide to pH 6.4, and 250 µg/ml 1 micron magnetic particles Sera-Mag™ MG-CM Carboxylate Modified (Seradyn, Inc.; Indianapolis, Ind.; Cat. No. 24152105-050450) having oligo(dT)$_{14}$ covalently bound thereto.

A "Wash Solution" contains 10 mM HEPES free acid, 6.5 mM sodium hydroxide, 1 mM EDTA free acid, 0.3% (v/v) ethyl alcohol absolute, 0.02% (w/v) methyl paraben, 0.01% (w/v) propyl paraben, 150 mM sodium chloride, 0.1% (w/v) lauryl sulfate, sodium (SDS), and 4 M sodium hydroxide to pH 7.5.

An "Amplification Reagent" is a lyophilized form of a 3.6 mL solution containing 26.7 mM rATP, 5.0 mM rCTP, 33.3 mM rGTP and 5.0 mM rUTP, 125 mM HEPES free acid, 8% (w/v) trehalose dihydrate, 1.33 mM dATP, 1.33 mM dCTP, 1.33 mM dGTP, 1.33 mM dTTP, and 4 M sodium hydroxide to pH 7.5. The Amplification Reagent is reconstituted in 9.7 mL of "Amplification Reagent Reconstitution Solution" described below.

An "Amplification Reagent Reconstitution Solution" contains 0.4% (v/v) ethyl alcohol absolute, 0.10% (w/v) methyl paraben, 0.02% (w/v) propyl paraben, 33 mM KCl, 30.6 mM MgCl$_2$, 0.003% phenol red.

A "Primer Reagent" contains 1 mM EDTA disodium dihydrate, ACS, 10 mM Trizma7 base, and 6M hydrochloric acid to pH 7.5.

An "Enzyme Reagent" is a lyophilized form of a 1.45 mL solution containing 20 mM HEPES free acid dihydrate, 125 mM N-acetyl-L-cysteine, 0.1 mM EDTA disodium dihydrate, 0.2% (v/v) TRITON® X-100 detergent, 0.2 M trehalose dihydrate, 0.90 RTU/mL Moloney murine leukemia virus ("MMLV") reverse transcriptase, 0.20 U/mL T7 RNA polymerase, and 4M sodium hydroxide to pH 7.0. (One "unit" or "RTU" of activity is defined as the synthesis and release of 5.75 fmol cDNA in 15 minutes at 37° C. for MMLV reverse transcriptase, and for T7 RNA polymerase, one "unit" or "U" of activity is defined as the production of 5.0 fmol RNA transcript in 20 minutes at 37° C.) The Enzyme Reagent is reconstituted in 3.6 mL of "Enzyme Reagent Reconstitution Solution" described below.

An "Enzyme Reagent Reconstitution Solution" contains 50 mM HEPES free acid, 1 mM EDTA free acid, 10% (v/v) TRITON X-100 detergent, 120 mM potassium chloride, 20% (v/v) glycerol anhydrous, and 4 M sodium hydroxide to pH 7.0.

A "Probe Reagent" is a lyophilized form of a 3.6 mL solution containing 110 mM lithium lauryl sulfate, 10 mM of mercaptoethane sulfonic acid, 100 mM lithium succinate, and 3% PVP. The Probe Reagent is reconstituted in 36 mL of "Probe Reagent Reconstitution Solution" described below.

A "Probe Reagent Reconstitution Solution" contains 100 mM succinic acid, 73 mM lithium lauryl sulfate, 100 mM lithium hydroxide monohydrate, 15 mM aldrithiol, 1.2 M lithium chloride, 20 mM EDTA, 3% (v/v) ethyl alcohol, and 2M lithium hydroxide to pH 4.7.

A "Selection Reagent" contains 600 mM boric acid, ACS, 182.5 mM sodium hydroxide, ACS, 1% (v/v) TRITON X-100 detergent, and 4 M sodium hydroxide to pH 8.5.

A "Detection Reagent" comprises Detect Reagent I, which contains 1 mM nitric acid and 32 mM hydrogen peroxide, 30% (v/v), and Detect Reagent II, which contains 1.5 M sodium hydroxide.

An "Oil Reagent" is a silicone oil.

Example 2

Initial Amplification Oligonucleotide Concentration Optimization

In this example, two amplification oligonucleotides (SEQ ID NOs. 15 and 18) specific for *Megasphaera elsdenii* were tested at three different concentrations (10, 20, 30 picomoles (pmol) per reaction) using 0, 1, 10, 100, 1000, and 10000 colony forming units (CFU) of *M. elsdenii* cells (ATCC No. 17752) per milliliter (mL) of Lysis Buffer. The first 27 bases of SEQ ID NO: 18 was a T7 promoter sequence. Additional oligonucleotides included two target capture probes (SEQ ID NOs. 1 and 2) and a detection probe (SEQ ID NO:24 with an acridinium esther (AE) incorporated using a linker positioned between bases 11 and 12). The amplification oligonucleotides were evaluated using (1) Target Capture, described in Weisburg et al., U.S. Pat. No. 6,110,678 (the contents of which are incorporated by reference herein); (2) Transcription-Mediated Amplification (TMA), described in Kacian et al. in U.S. Pat. Nos. 5,399,491 and 5,480,784 (the contents of which are incorporated by reference herein) and by Lee et al., supra, ch. 8; and (3) Hybridization Protection Assay (HPA), described in Arnold et al., U.S. Pat. No. 5,283,174 (the contents of which are incorporated by reference herein). The protocols for each method are briefly described below.

*Megasphaera elsdenii* were lysed in Lysis Buffer and diluted with Lysis Buffer to 10000, 1000, 100, 1, and 0 CFU per mL and 400 µL of each concentration were placed in separate 12 mm×75 mm tubes. Target Capture Reagent, 100 µL containing 2 picomoles (pmol) of SEQ ID Nos. 1 and 2, was added to each tube and the tubes were covered and incubated at 62° C. for 30 minutes to immobilize the IVT, if present, on the magnetic beads. The magnetic beads were pelleted using a DTS® 400 Target Capture System (Gen-Probe; Cat. No. 104555) and the supernatant was aspirated. The magnetic beads were resuspended in 1 mL of Wash Solution, re-pelletted and the Wash Solution was aspirated. The magnetic beads were resuspended in 75 µL of reconstituted Amplification Reagent containing 10, 20, or 30 pmol of SEQ ID NOs. 15 and 18. Oil Reagent (200 µL) was added to prevent evaporation and the tubes were covered and incubated at 62° C. for 10 minutes to disrupt secondary structures of the transcripts and allow the primer to bind. The tubes were then incubated at 42° C. for 5 minutes to bring them to the appropriate temperature for the enzymes. Reconstituted Enzyme Reagent (25 µL) was added and the tubes were incubated at 42° C. for 60 minutes to allow the enzymes to amplify the target nucleic acid. Probe Reagent (1004) containing Xe6 RLU of the detection probe (SEQ ID NO:24 with an acridinium esther (AE) incorporated using a linker positioned between bases 11 and 12) was added to each tube. The tubes were briefly vortexed, covered, and incubated at 62° C. for 20 minutes to allow the probe to hybridize to the amplified nucleic acid. The tubes were incubated at room temperature for 5 minutes. Label on the non-hybridized probes was inactivated by adding 2504 of Selection Reagent and incubating at 62° C. for 10 minutes. The tubes were cooled at room temperature for 15 minutes. The tubes were analyzed in a LEADER® luminometer capable of automatically injecting 200 µL of Detect Reagent I, followed by 200 of Detect Reagent II, and then repeatedly reading the emission light in the tubes. Five replicates were run for each primer concentration at each *M. elsdenii* concentration. The results were measured in relative light units (RLU) and a minimum of 100,000 RLU was the threshold for a test to be considered positive. The results are summarized in Table 1, below and indicate an increase in primer concentration increased the sensitivity of the assay.

TABLE 1

| Amt. of M. elsdenii | Amt. of Primer | Ave. RFU | % CV |
|---|---|---|---|
| 0 CFU/mL | 10 pmol/rxn | 6,246 | 59.3 |
| 1 CFU/mL | 10 pmol/rxn | 11,996 | 15.9 |
| 10 CFU/mL | 10 pmol/rxn | 121,215 | 36.8 |
| 100 CFU/mL | 10 pmol/rxn | 26,931 | 21.1 |
| 1000 CFU/mL | 10 pmol/rxn | 45,251 | 14.4 |
| 10000 CFU/mL | 10 pmol/rxn | 118,891 | 16.5 |
| 0 CFU/mL | 20 pmol/rxn | 3,332 | 7.6 |
| 1 CFU/mL | 20 pmol/rxn | 14,358 | 17.7 |
| 10 CFU/mL | 20 pmol/rxn | 30,982 | 54.6 |
| 100 CFU/mL | 20 pmol/rxn | 58,673 | 22.6 |
| 1000 CFU/mL | 20 pmol/rxn | 137,117 | 3.1 |
| 10000 CFU/mL | 20 pmol/rxn | 376,183 | 9.1 |
| 0 CFU/mL | 30 pmol/rxn | 3,654 | 7.5 |
| 1 CFU/mL | 30 pmol/rxn | 14,575 | 39.2 |
| 10 CFU/mL | 30 pmol/rxn | 33,111 | 38.2 |
| 100 CFU/mL | 30 pmol/rxn | 113,825 | 29.9 |
| 1000 CFU/mL | 30 pmol/rxn | 310,468 | 14.4 |
| 10000 CFU/mL | 30 pmol/rxn | 656,873 | 7.8 |

Example 3

Refined Amplification Oligonucleotide Concentration Optimization

In this example, the concentrations of the two amplification oligonucleotides (SEQ ID NOs. 15 and 18) described in Example 2 were further optimized. The target capture probes, detection probe, and procedures were also the same as those described in Example 2. The concentration of each amplification oligonucleotide ranged from 12 pmol per reaction to 53 pmol per reaction. The amplification oligonucleotides were evaluated using *M. elsdenii* cells (ATCC No. 17752) at 1000 CFU per mL of Lysis Buffer. The negative control contained 30 pmol per reaction of each amplification oligonucleotide and Lysis Buffer without any bacteria cells. Five replicates were tested for each prime concentration combination and ten replicates were tested for the negative control. The results are summarized in Table 2, below and indicate that the optimal primer concentrations were 22.5 pmol per reaction for SEQ ID NO:18 and 53 pmol per reaction for SEQ ID NO:15.

TABLE 2

| Amt. SEQ ID NO: 15 | Amt. SEQ ID NO: 18 | Ave. RFU | % CV |
|---|---|---|---|
| Negative Control | | 4,893 | 10.8 |
| 15 pmol/rxn | 15 pmol/rxn | 213,098 | 23.5 |
| 15 pmol/rxn | 30 pmol/rxn | 773,957 | 16.1 |
| 30 pmol/rxn | 15 pmol/rxn | 96,793 | 25.2 |
| 30 pmol/rxn | 30 pmol/rxn | 508,003 | 2433 |
| 22.5 pmol/rxn | 19 pmol/rxn | 171,179 | 1539 |
| 22.5 pmol/rxn | 53 pmol/rxn | 1,997,576 | 11.4 |

TABLE 2-continued

| Amt. SEQ ID NO: 15 | Amt. SEQ ID NO: 18 | Ave. RFU | % CV |
|---|---|---|---|
| 11.89 pmol/rxn | 14 pmol/rxn | 120,375 | 23.5 |
| 33.11 pmol/rxn | 14 pmol/rxn | 76,395 | 21.8 |
| 22.5 pmol/rxn | 22.5 pmol/rxn | 215,109 | 19.1 |

Example 4

Sensitivity

In this example, the sensitivity of two capture probes (SEQ ID NOs. 1 and 2), two amplification oligonucleotides (SEQ ID Nos. 15 and 18), and a detection probe (SEQ ID NO:24 with an AE incorporated using a linker positioned between bases 11 and 12) was evaluated using 0, 0.1, 1, 10, 100, and 1000 CFU per mL of *M. elsdenii* cells. The procedures were the same as those described in Example 2 with the following changes. The concentration of SEQ ID NO:15 was 50 pmol per reaction and the concentration of SEQ ID NO:18 was 20 pmol per reaction. The results are summarized in Table 3, below and indicate that the set of oligonucleotides were able to detect 100 CFU per mL of *M. elsdenii* cells.

TABLE 3

| Amt. M. elsdenii | Ave. RFU | % CV |
|---|---|---|
| 0 CFU/mL | 3265 | 11.2 |
| 0.1 CFU/mL | 15391 | 64.7 |
| 1 CFU/mL | 46316 | 59.9 |
| 10 CFU/mL | 141055 | 37.3 |
| 100 CFU/mL | 385902 | 6.2 |
| 1000 CFU/mL | 820594 | 6.3 |

Example 5

Spiked Clinical Samples

In this example, the ability of two capture probes (SEQ ID Nos. 1 and 2), two amplification oligonucleotides (SEQ ID Nos. 15 and 18), and a detection probe (SEQ ID NO:24 with an AE incorporated using a linker positioned between bases 11 and 12) to detect *M. elsdenii* cells spiked into clinical samples was evaluated. Swab samples were collected from female volunteers and stored in Lysis Buffer. The swab samples were initially screened for X and divided into two pools based on the initial screening. The pooled samples were spiked with *M. elsdenii* cells at 0, 1, 10, 100, and 1000 CFU per mL. The procedures were the same as those described in Example 2 with the following changes. The concentration of SEQ ID NO:15 was 50 pmol per reaction and the concentration of SEQ ID NO:18 was 20 pmol per reaction. The results are summarized in Table 4, below and indicate that the set of oligonucleotides were able to detect 100 CFU per mL of *M. elsdenii* cells spiked into clinical samples.

TABLE 4

| Pool | Amt. M. elsdenii | Ave. RFU | % CV |
|---|---|---|---|
| 1 | 0 | 40,587 | 71.2 |
| | 1 | 27,313 | 15.7 |
| | 10 | 124,071 | 48.6 |
| | 100 | 277,937 | 35.6 |
| | 100 | 751,671 | 5.3 |

TABLE 4-continued

| Pool | Amt. M. elsdenii | Ave. RFU | % CV |
|---|---|---|---|
| 2 | 0 | 34,479 | 24.0 |
|  | 1 | 35,774 | 34.4 |
|  | 10 | 53,906 | 11.3 |
|  | 100 | 204,007 | 8.7 |
|  | 100 | 796,224 | 3.7 |

From the foregoing, it will be appreciated that, although specific embodiments of the invention have been described herein for purposes of illustration, various modifications may be made without deviating from the spirit and scope of the invention. Accordingly, the invention is not limited except as by the appended claims. All publications, patents, and patent applications cited herein are hereby incorporated by reference in their entireties for all purposes.

Example 5

Exemplary Oligomer Sequences

In this example, there is provided a list of oligonucleotide sequences drafted with a 5' to 3' in orientation. (Table 5). Underlined sequence text represents exemplary tail sequences configured to hybridize with an immobilized probe. Bolded sequence text represents exemplary promoter sequences for promoter-based amplification oligomers. Pseudotarget (has primer binding sites but no probe binding sites).

TABLE 5

| SEQ ID NO: | Sequence | Description |
|---|---|---|
| 1 | CTACTGCTGCCTCCCGTAGGAGTTTAAA AAAAAAAAAAAAAAAAAAAAAAAAAAAA | Target capture oligomer (universal - also captures Atopobium vaginae) |
| 2 | GGACTACCAGGGTATCTAATCCTGTTTA AAAAAAAAAAAAAAAAAAAAAAAAAAAA | Target capture oligomer (universal - also captures Atopobium vaginae) |
| 3 | CGACACGAGCTGACGACAGCCATGCATTT AAAAAAAAAAAAAAAAAAAAAAAAAAAA | Target cappure oligomer |
| 4 | GACGTCATCCCCACCTTCCTTTTAAAAAA AAAAAAAAAAAAAAAAAAAAA | Target capture oligomer |
| 5 | CGTATTCGGTATTAGCAGCCGTTTAAAAA AAAAAAAAAAAAAAAAAAAAAA | Target capture oligomer |
| 6 | GCTGGCACGTAGTTAGCCGTGGCTTTTAA AAAAAAAAAAAAAAAAAAAAAAAAAAAA | Target capture oligomer |
| 7 | CTACTGCTGCCTCCCGTAGGAG | Target hybridizing sequence (THS for SEQ ID NO: 1) |
| 8 | GGACTACCAGGGTATCTAATCCTG | Target hybridizing sequence (THS for SEQ ID NO: 2) |
| 9 | CGACACGAGCTGACGACAGCCATGCA | Target hybridizing sequence (THS for SEQ ID NO: 3) |
| 10 | GACGTCATCCCCACCTTCCT | Target hybridizing sequence (THS for SEQ ID NO: 4) |
| 11 | CGTATTCGGTATTAGCAGCCG | Target hybridizing sequence (THS for SEQ ID NO: 5) |
| 12 | GCTGGCACGTAGTTAGCCGTGGCT | Target hybridizing sequence (THS for SEQ ID NO: 6) |
| 13 | GTAACGGCCCAACAAGGCGA | Non-T7 primer |
| 14 | GCCCAACAAGGCGATGATCAG | Non-T7 primer |
| 15 | CTGTTATACGGGACGAAT | Non-T7 primer |
| 16 | AATTTAATACGACTCACTATAGGGAGAGTAG GAGTCTGGGCCGTGTCTCAG | T7 amp oligo |
| 17 | AATTTAATACGACTCACTATAGGGAGACGTA GGAGTCTGGGCCGTGTCTC | T7 amp oligo |
| 18 | AATTTAATACGACTCACTATAGGGAGACCGC ACTTTTAAGACCGACTTA | T7 amp oligo |
| 19 | GTAGGAGTCTGGGCCGTGTCTCAG | Target hybridizing sequence (THS for SEQ ID NO: 16) |
| 20 | CGTAGGAGTCTGGGCCGTGTCTC | Target hybridizing sequence (THS for SEQ ID NO: 17) |
| 21 | CCGCACTTTTAAGACCGACTTA | Target hybridizing sequence (THS for SEQ ID NO: 18) |

TABLE 5-continued

| SEQ ID NO: | Sequence | Description |
|---|---|---|
| 22 | AATTTAATACGACTCACTATAGGGAGA | T7 promoter sequence |
| 23 | CAGTAGCCGGTCTGAGAGGATGA | Detection probe |
| 24 | GACGGTACCGTAAGAGAAAGCC | Detection probe |
| 25 | GTAGCCGGTCTGAGAGGATGAACG | Detection probe |
| 26 | CGGTACCGTAAGAGAAAG | Detection probe |
| 27 | CTGTTATACGGGACGAATTAAGTCGGTCTTAAAAGTGCGG | Pseudotarget |
| 28 | GCCCARCAAGGCGA | Core primer sequence |
| 29 | GTNACGGCCCARCAAGGCGAKGATCAG | Primer regions |
| 30 | GTAGCCGGTCTGAGAGGATGA | Core probe sequence |
| 31 | CAGTAGCCGGTCTGAGAGGATGAACG | Probe region |
| 32 | GTAGGAGTNTGGGCCGTGTCTC | Core primer sequence |
| 33 | CGTAGGAGTNTGGGCCGTGTCTCAG | Primer region |
| 34 | AGTTGGAGGGGTAACGGCCCAACAAGGCGATGATCAG | Extended primer region |
| 35 | GAGTNTGGGCCGTG | Truncated core primer sequence |
| 36 | CCTCCCGTAGGAGTNTGGGCCGTGTCTCAGTCCC | Extended primer region |
| 37 | CTGTTATACGGGAC | Core primer sequence |
| 38 | GGTTGTAAAGTTCTGTTATACGGGACGAATGG | Primer region |
| 39 | CTTTTAAGACCGAC | Core primer sequence |
| 40 | GCCCCGCACTTTTAAGACCGACTTACGACGC | Primer region |
| 41 | GTAACGGCCCAACAAGGCGACTGAGACACGGCCCAGACTCCTAC | Pseudotarget |
| 42 | GTAACGGCCCAACAAGGCGAGAGACACGGCCCAGACTCCTACG | Pseudotarget |
| 43 | GCCCAACAAGGCGATGATCAGCTGAGACACGGCCCAGACTCCTAC | Pseudotarget |
| 44 | GCCCAACAAGGCGATGATCAGGAGACACGGCCCAGACTCCTACG | Pseudotarget |

What is claimed is:

1. A combination of at least two oligomers for detecting in a sample a *Megasphaera* sp. 16S rRNA or a gene encoding a *Megasphaera* sp. 16S rRNA, said oligomer combination comprising:
 a first amplification oligomer comprising a first target-hybridizing sequence consisting of 14 to 32 contiguous nucleotides contained in the sequence of SEQ ID NO: 38 and that includes at least the sequence of SEQ ID NO: 37; and
 a second amplification oligomer that is a promoter primer comprising
 (i) a second target-hybridizing sequence consisting of 22 to 31 contiguous nucleotides contained in the sequence of SEQ ID NO: 40 and that includes at least the sequence of SEQ ID NO: 21 and
 (ii) a T7 promoter sequence located 5' to the second target-hybridizing sequence.

2. The combination of at least two oligomers of claim 1, wherein the oligomers are contained in a kit for the detection of a *Megasphaera* sp. target nucleic acid.

3. A reaction mixture comprising the combination of at least two oligomers of claim 1.

4. The combination of claim 1, wherein the first target hybridizing sequence consists of the sequence of SEQ ID NO:15 and the second target hybridizing sequence consists of the sequence of SEQ ID NO:21.

5. A method for detecting in a sample a *Megasphaera* sp. target nucleic acid, wherein the target nucleic acid is a *Megasphaera* sp. 16S rRNA or a gene encoding said 16S rRNA, said method comprising:
 (a) providing a sample, wherein said sample is suspected of containing a *Megasphaera* sp. bacterium;
 (b) contacting said sample with at least two oligomers for amplifying a *Megasphaera* sp. nucleic acid target region corresponding to the target nucleic acid, said at least two oligomers comprising
 a first amplification oligomer comprising
 a first target-hybridizing sequence consisting of 14 to 32 contiguous nucleotides contained in the sequence of SEQ ID NO:38 and that includes at least the sequence of SEQ ID NO: 37; and
 a second amplification oligomer comprising
 a second target-hybridizing sequence consisting of 22 to 31 contiguous nucleotides contained in the sequence of SEQ ID NO: 40 and that includes at least the sequence shown in SEQ ID NO: 21;
 (c) performing an in vitro nucleic acid amplification reaction, wherein any *Megasphaera* target nucleic acid present in said sample is used as a template for generating an amplification product; and
 (d) detecting the presence or absence of the amplification product, thereby indicating the presence or absence of *Megasphaera* sp. in said sample.

6. The method of claim 5, wherein the second amplification oligomer is a promoter primer further comprising a promoter sequence located 5' to the target-hybridizing sequence, and optionally wherein the promoter sequence is a T7 promoter sequence or SEQ ID NO:22.

7. The method of claim 6, wherein the second amplification oligomer has the sequence shown in SEQ ID NO:18.

8. The method of claim 5, further comprising purifying the *Megasphaera* target nucleic acid from other components in the sample before step (b), wherein, optionally, the purifying step comprises contacting the sample with at least one capture probe oligomer comprising (i) a target-hybridizing sequence covalently attached to a sequence or moiety that binds to an immobilized probe, wherein said target-hybridizing sequence is selected from the group consisting of SEQ ID NOs:7-12; or (ii) a sequence selected from the group consisting of SEQ ID NOs:1-6.

9. The method of claim 5, wherein the detecting step (d) comprises contacting said in vitro nucleic acid amplification reaction with a detection probe oligomer configured to specifically hybridize to the amplification product under conditions whereby the presence or absence of the amplification product is determined, thereby indicating the presence or absence of *Megasphaera* sp. in said sample.

10. The method of claim 9, wherein the detection probe oligomer comprises a target-hybridizing sequence that is from 14 to 40 nucleotides in length and is configured to specifically hybridize to a target sequence contained within SEQ ID NO:45 from nucleotide position 466 to nucleotide position 607.

11. The method of claim 10, wherein the detection probe target-hybridizing sequence is contained in the sequence of SEQ ID NO:24 and includes at least the sequence of SEQ ID NO:26.

12. The method of claim 11, wherein the detection probe target-hybridizing sequence is selected from the group consisting of SEQ ID NO:24 and SEQ ID NO:26.

13. The method of claim 9, further comprising contacting the sample with a pseudotarget oligomer that can be amplified, using the first and second amplification oligomers, in the in vitro nucleic acid amplification reaction to generate a second amplification product that does not specifically hybridize to the detection probe under the detection reaction conditions, wherein the pseudotarget oligomer has a sequence selected from the group consisting of SEQ ID NO:41, SEQ ID NO:42, SEQ ID NO:43, and SEQ ID NO:44.

14. The method of claim 9, wherein the detection probe comprises a label selected from the group consisting of
 (a) a chemiluminescent label;
 (b) a fluorescent label;
 (c) a quencher; and
 (d) a combination of one or more of (a), (b), and (c).

15. The method of claim 9, wherein the detecting step (d) occurs during the amplifying step (c).

16. The method of claim 9, wherein the detection probe further comprises a non-target-hybridizing sequence, and, optionally, the detection probe is a hairpin detection probe, a molecular beacon or a molecular torch.

17. The method of claim 5, wherein the amplification reaction at step (c) is an isothermal amplification reaction or a real-time isothermal amplification reaction.

18. The method of claim 5, wherein the first target hybridizing sequence consists of the sequence of SEQ ID NO: 15 and the second target hybridizing sequence consists of the sequence of SEQ ID NO: 21.

* * * * *

SEQUENCE LISTING

```
<160> NUMBER OF SEQ ID NOS: 45

<210> SEQ ID NO 1
<211> LENGTH: 55
<212> TYPE: DNA
<213> ORGANISM: Artificial Sequence
<220> FEATURE:
<223> OTHER INFORMATION: Synthetic Oligonucleotide Sequence
<220> FEATURE:
<221> NAME/KEY: capture-tail
<222> LOCATION: (23)..(55)

<400> SEQUENCE: 1
ctactgctgc ctcccgtagg agtttaaaaa aaaaaaaaaa aaaaaaaaaa aaaaa         55

<210> SEQ ID NO 2
<211> LENGTH: 57
<212> TYPE: DNA
<213> ORGANISM: Artificial Sequence
<220> FEATURE:
<223> OTHER INFORMATION: Synthetic Oligonucleotide Sequence
<220> FEATURE:
<221> NAME/KEY: capture-tail
<222> LOCATION: (25)..(57)

<400> SEQUENCE: 2
ggactaccag ggtatctaat cctgtttaaa aaaaaaaaaa aaaaaaaaa aaaaaaa         57

<210> SEQ ID NO 3
```

-continued

```
<211> LENGTH: 59
<212> TYPE: DNA
<213> ORGANISM: Artificial Sequence
<220> FEATURE:
<223> OTHER INFORMATION: Synthetic Oligonucleotide Sequence
<220> FEATURE:
<221> NAME/KEY: capture-tail
<222> LOCATION: (27)..(59)

<400> SEQUENCE: 3
cgacacgagc tgacgacagc catgcattta aaaaaaaaaa aaaaaaaaaa aaaaaaaa      59

<210> SEQ ID NO 4
<211> LENGTH: 53
<212> TYPE: DNA
<213> ORGANISM: Artificial Sequence
<220> FEATURE:
<223> OTHER INFORMATION: Synthetic Oligonucleotide Sequence
<220> FEATURE:
<221> NAME/KEY: capture-tail
<222> LOCATION: (21)..(53)

<400> SEQUENCE: 4
gacgtcatcc ccaccttcct tttaaaaaaa aaaaaaaaaa aaaaaaaaaa aaa            53

<210> SEQ ID NO 5
<211> LENGTH: 54
<212> TYPE: DNA
<213> ORGANISM: Artificial Sequence
<220> FEATURE:
<223> OTHER INFORMATION: Synthetic Oligonucleotide Sequence
<220> FEATURE:
<221> NAME/KEY: capture-tail
<222> LOCATION: (22)..(54)

<400> SEQUENCE: 5
cgtattcggt attagcagcc gtttaaaaaa aaaaaaaaaa aaaaaaaaaa aaaa           54

<210> SEQ ID NO 6
<211> LENGTH: 57
<212> TYPE: DNA
<213> ORGANISM: Artificial Sequence
<220> FEATURE:
<223> OTHER INFORMATION: Synthetic Oligonucleotide Sequence
<220> FEATURE:
<221> NAME/KEY: capture-tail
<222> LOCATION: (25)..(57)

<400> SEQUENCE: 6
gctggcacgt agttagccgt ggcttttaaa aaaaaaaaaa aaaaaaaaaa aaaaaaa        57

<210> SEQ ID NO 7
<211> LENGTH: 22
<212> TYPE: DNA
<213> ORGANISM: Artificial Sequence
<220> FEATURE:
<223> OTHER INFORMATION: Synthetic Oligonucleotide Sequence

<400> SEQUENCE: 7
ctactgctgc ctcccgtagg ag                                             22

<210> SEQ ID NO 8
<211> LENGTH: 24
<212> TYPE: DNA
<213> ORGANISM: Artificial Sequence
<220> FEATURE:
<223> OTHER INFORMATION: Synthetic Oligonucleotide Sequence

<400> SEQUENCE: 8
```

```
ggactaccag ggtatctaat cctg                                              24

<210> SEQ ID NO 9
<211> LENGTH: 26
<212> TYPE: DNA
<213> ORGANISM: Artificial Sequence
<220> FEATURE:
<223> OTHER INFORMATION: Synthetic Oligonucleotide Sequence

<400> SEQUENCE: 9
cgacacgagc tgacgacagc catgca                                            26

<210> SEQ ID NO 10
<211> LENGTH: 20
<212> TYPE: DNA
<213> ORGANISM: Artificial Sequence
<220> FEATURE:
<223> OTHER INFORMATION: Synthetic Oligonucleotide Sequence

<400> SEQUENCE: 10
gacgtcatcc ccaccttcct                                                   20

<210> SEQ ID NO 11
<211> LENGTH: 21
<212> TYPE: DNA
<213> ORGANISM: Artificial Sequence
<220> FEATURE:
<223> OTHER INFORMATION: Synthetic Oligonucleotide Sequence

<400> SEQUENCE: 11
cgtattcggt attagcagcc g                                                 21

<210> SEQ ID NO 12
<211> LENGTH: 24
<212> TYPE: DNA
<213> ORGANISM: Artificial Sequence
<220> FEATURE:
<223> OTHER INFORMATION: Synthetic Oligonucleotide Sequence

<400> SEQUENCE: 12
gctggcacgt agttagccgt ggct                                              24

<210> SEQ ID NO 13
<211> LENGTH: 20
<212> TYPE: DNA
<213> ORGANISM: Artificial Sequence
<220> FEATURE:
<223> OTHER INFORMATION: Synthetic Oligonucleotide Sequence

<400> SEQUENCE: 13
gtaacggccc aacaaggcga                                                   20

<210> SEQ ID NO 14
<211> LENGTH: 21
<212> TYPE: DNA
<213> ORGANISM: Artificial Sequence
<220> FEATURE:
<223> OTHER INFORMATION: Synthetic Oligonucleotide Sequence

<400> SEQUENCE: 14
gcccaacaag gcgatgatca g                                                 21

<210> SEQ ID NO 15
<211> LENGTH: 18
<212> TYPE: DNA
```

```
<213> ORGANISM: Artificial Sequence
<220> FEATURE:
<223> OTHER INFORMATION: Synthetic Oligonucleotide Sequence

<400> SEQUENCE: 15
ctgttatacg ggacgaat                                                  18

<210> SEQ ID NO 16
<211> LENGTH: 51
<212> TYPE: DNA
<213> ORGANISM: Artificial Sequence
<220> FEATURE:
<223> OTHER INFORMATION: Synthetic Oligonucleotide Sequence
<220> FEATURE:
<221> NAME/KEY: promoter
<222> LOCATION: (1)..(27)

<400> SEQUENCE: 16
aatttaatac gactcactat agggagagta ggagtctggg ccgtgtctca g             51

<210> SEQ ID NO 17
<211> LENGTH: 50
<212> TYPE: DNA
<213> ORGANISM: Artificial Sequence
<220> FEATURE:
<223> OTHER INFORMATION: Synthetic Oligonucleotide Sequence
<220> FEATURE:
<221> NAME/KEY: promoter
<222> LOCATION: (1)..(27)

<400> SEQUENCE: 17
aatttaatac gactcactat agggagacgt aggagtctgg gccgtgtctc               50

<210> SEQ ID NO 18
<211> LENGTH: 49
<212> TYPE: DNA
<213> ORGANISM: Artificial Sequence
<220> FEATURE:
<223> OTHER INFORMATION: Synthetic Oligonucleotide Sequence
<220> FEATURE:
<221> NAME/KEY: promoter
<222> LOCATION: (1)..(27)

<400> SEQUENCE: 18
aatttaatac gactcactat agggagaccg cacttttaag accgactta                49

<210> SEQ ID NO 19
<211> LENGTH: 24
<212> TYPE: DNA
<213> ORGANISM: Artificial Sequence
<220> FEATURE:
<223> OTHER INFORMATION: Synthetic Oligonucleotide Sequence

<400> SEQUENCE: 19
gtaggagtct gggccgtgtc tcag                                           24

<210> SEQ ID NO 20
<211> LENGTH: 23
<212> TYPE: DNA
<213> ORGANISM: Artificial Sequence
<220> FEATURE:
<223> OTHER INFORMATION: Synthetic Oligonucleotide Sequence

<400> SEQUENCE: 20
cgtaggagtc tgggccgtgt ctc                                            23

<210> SEQ ID NO 21
```

```
<211> LENGTH: 22
<212> TYPE: DNA
<213> ORGANISM: Artificial Sequence
<220> FEATURE:
<223> OTHER INFORMATION: Synthetic Oligonucleotide Sequence

<400> SEQUENCE: 21
ccgcactttt aagaccgact ta                                          22

<210> SEQ ID NO 22
<211> LENGTH: 27
<212> TYPE: DNA
<213> ORGANISM: Artificial Sequence
<220> FEATURE:
<223> OTHER INFORMATION: Synthetic Oligonucleotide Sequence

<400> SEQUENCE: 22
aatttaatac gactcactat agggaga                                     27

<210> SEQ ID NO 23
<211> LENGTH: 23
<212> TYPE: DNA
<213> ORGANISM: Artificial Sequence
<220> FEATURE:
<223> OTHER INFORMATION: Synthetic Oligonucleotide Sequence

<400> SEQUENCE: 23
cagtagccgg tctgagagga tga                                         23

<210> SEQ ID NO 24
<211> LENGTH: 22
<212> TYPE: DNA
<213> ORGANISM: Artificial Sequence
<220> FEATURE:
<223> OTHER INFORMATION: Synthetic Oligonucleotide Sequence

<400> SEQUENCE: 24
gacggtaccg taagagaaag cc                                          22

<210> SEQ ID NO 25
<211> LENGTH: 24
<212> TYPE: DNA
<213> ORGANISM: Artificial Sequence
<220> FEATURE:
<223> OTHER INFORMATION: Synthetic Oligonucleotide Sequence

<400> SEQUENCE: 25
gtagccggtc tgagaggatg aacg                                        24

<210> SEQ ID NO 26
<211> LENGTH: 18
<212> TYPE: DNA
<213> ORGANISM: Artificial Sequence
<220> FEATURE:
<223> OTHER INFORMATION: Synthetic Oligonucleotide Sequence

<400> SEQUENCE: 26
cggtaccgta agagaaag                                               18

<210> SEQ ID NO 27
<211> LENGTH: 40
<212> TYPE: DNA
<213> ORGANISM: Artificial Sequence
<220> FEATURE:
<223> OTHER INFORMATION: Synthetic Oligonucleotide Sequence

<400> SEQUENCE: 27
```
ctgttatacg ggacgaatta agtcggtctt aaaagtgcgg                          40

<210> SEQ ID NO 28
<211> LENGTH: 14
<212> TYPE: DNA
<213> ORGANISM: Artificial Sequence
<220> FEATURE:
<223> OTHER INFORMATION: Synthetic Oligonucleotide Sequence
<220> FEATURE:
<221> NAME/KEY: misc_feature
<222> LOCATION: (6)..(6)
<223> OTHER INFORMATION: g or a.  purine

<400> SEQUENCE: 28
gcccarcaag gcga                                                     14

<210> SEQ ID NO 29
<211> LENGTH: 27
<212> TYPE: DNA
<213> ORGANISM: Artificial Sequence
<220> FEATURE:
<223> OTHER INFORMATION: Synthetic Oligonucleotide Sequence
<220> FEATURE:
<221> NAME/KEY: misc
<222> LOCATION: (3)..(3)
<223> OTHER INFORMATION: a or g or c or t/u or unknown or other. any.
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc
<222> LOCATION: (12)..(12)
<223> OTHER INFORMATION: g or a.  purine
<220> FEATURE:
<221> NAME/KEY: misc
<222> LOCATION: (21)..(21)
<223> OTHER INFORMATION: g or t/u.  keto.

<400> SEQUENCE: 29
gtnacggccc arcaaggcga kgatcag                                       27

<210> SEQ ID NO 30
<211> LENGTH: 21
<212> TYPE: DNA
<213> ORGANISM: Artificial Sequence
<220> FEATURE:
<223> OTHER INFORMATION: Synthetic Oligonucleotide Sequence

<400> SEQUENCE: 30
gtagccggtc tgagaggatg a                                             21

<210> SEQ ID NO 31
<211> LENGTH: 26
<212> TYPE: DNA
<213> ORGANISM: Artificial Sequence
<220> FEATURE:
<223> OTHER INFORMATION: Synthetic Oligonucleotide Sequence

<400> SEQUENCE: 31
cagtagccgg tctgagagga tgaacg                                        26

<210> SEQ ID NO 32
<211> LENGTH: 22
<212> TYPE: DNA
<213> ORGANISM: Artificial Sequence
<220> FEATURE:
<223> OTHER INFORMATION: Synthetic Oligonucleotide Sequence
<220> FEATURE:

```
<221> NAME/KEY: misc
<222> LOCATION: (9)..(9)
<223> OTHER INFORMATION: a or g or c or t/u or unknown or other. any.
<220> FEATURE:
<221> NAME/KEY: misc_feature
<222> LOCATION: (9)..(9)
<223> OTHER INFORMATION: n is a, c, g, or t

<400> SEQUENCE: 32
gtaggagtnt gggccgtgtc tc                                              22

<210> SEQ ID NO 33
<211> LENGTH: 25
<212> TYPE: DNA
<213> ORGANISM: Artificial Sequence
<220> FEATURE:
<223> OTHER INFORMATION: Synthetic Oligonucleotide Sequence
<220> FEATURE:
<221> NAME/KEY: misc
<222> LOCATION: (10)..(10)
<223> OTHER INFORMATION: a or g or c or t/u or unknown or other. any.
<220> FEATURE:
<221> NAME/KEY: misc_feature
<222> LOCATION: (10)..(10)
<223> OTHER INFORMATION: n is a, c, g, or t

<400> SEQUENCE: 33
cgtaggagtn tgggccgtgt ctcag                                           25

<210> SEQ ID NO 34
<211> LENGTH: 37
<212> TYPE: DNA
<213> ORGANISM: Artificial Sequence
<220> FEATURE:
<223> OTHER INFORMATION: Synthetic Oligonucleotide Sequence

<400> SEQUENCE: 34
agttggaggg gtaacggccc aacaaggcga tgatcag                              37

<210> SEQ ID NO 35
<211> LENGTH: 14
<212> TYPE: DNA
<213> ORGANISM: Artificial Sequence
<220> FEATURE:
<223> OTHER INFORMATION: Synthetic Oligonucleotide Sequence
<220> FEATURE:
<221> NAME/KEY: misc
<222> LOCATION: (5)..(5)
<223> OTHER INFORMATION: a or g or c or t/u or unknown or other. any.
<220> FEATURE:
<221> NAME/KEY: misc_feature
<222> LOCATION: (5)..(5)
<223> OTHER INFORMATION: n is a, c, g, or t

<400> SEQUENCE: 35
gagtntgggc cgtg                                                       14

<210> SEQ ID NO 36
<211> LENGTH: 34
<212> TYPE: DNA
<213> ORGANISM: Artificial Sequence
<220> FEATURE:
<223> OTHER INFORMATION: Synthetic Oligonucleotide Sequence
<220> FEATURE:
<221> NAME/KEY: misc
<222> LOCATION: (15)..(15)
<223> OTHER INFORMATION: a or g or c or t/u or unknown or other. any.
<220> FEATURE:
<221> NAME/KEY: misc_feature
<222> LOCATION: (15)..(15)
<223> OTHER INFORMATION: n is a, c, g, or t
```

```
<400> SEQUENCE: 36
cctcccgtag gagtntgggc cgtgtctcag tccc                          34

<210> SEQ ID NO 37
<211> LENGTH: 14
<212> TYPE: DNA
<213> ORGANISM: Artificial Sequence
<220> FEATURE:
<223> OTHER INFORMATION: Synthetic Oligonucleotide Sequence

<400> SEQUENCE: 37
ctgttatacg ggac                                                14

<210> SEQ ID NO 38
<211> LENGTH: 32
<212> TYPE: DNA
<213> ORGANISM: Artificial Sequence
<220> FEATURE:
<223> OTHER INFORMATION: Synthetic Oligonucleotide Sequence

<400> SEQUENCE: 38
ggttgtaaag ttctgttata cgggacgaat gg                            32

<210> SEQ ID NO 39
<211> LENGTH: 14
<212> TYPE: DNA
<213> ORGANISM: Artificial Sequence
<220> FEATURE:
<223> OTHER INFORMATION: Synthetic Oligonucleotide Sequence

<400> SEQUENCE: 39
cttttaagac cgac                                                14

<210> SEQ ID NO 40
<211> LENGTH: 31
<212> TYPE: DNA
<213> ORGANISM: Artificial Sequence
<220> FEATURE:
<223> OTHER INFORMATION: Synthetic Oligonucleotide Sequence

<400> SEQUENCE: 40
gccccgcact tttaagaccg acttacgacg c                             31

<210> SEQ ID NO 41
<211> LENGTH: 44
<212> TYPE: DNA
<213> ORGANISM: Artificial Sequence
<220> FEATURE:
<223> OTHER INFORMATION: Synthetic Oligonucleotide Sequence

<400> SEQUENCE: 41
gtaacggccc aacaaggcga ctgagacacg gcccagactc ctac               44

<210> SEQ ID NO 42
<211> LENGTH: 43
<212> TYPE: DNA
<213> ORGANISM: Artificial Sequence
<220> FEATURE:
<223> OTHER INFORMATION: Synthetic Oligonucleotide Sequence

<400> SEQUENCE: 42
gtaacggccc aacaaggcga gagacacggc ccagactcct acg                43

<210> SEQ ID NO 43
```

<210> SEQ ID NO 43
<211> LENGTH: 45
<212> TYPE: DNA
<213> ORGANISM: Artificial Sequence
<220> FEATURE:
<223> OTHER INFORMATION: Synthetic Oligonucleotide Sequence

<400> SEQUENCE: 43
gcccaacaag gcgatgatca gctgagacac ggcccagact cctac                45

<210> SEQ ID NO 44
<211> LENGTH: 44
<212> TYPE: DNA
<213> ORGANISM: Artificial Sequence
<220> FEATURE:
<223> OTHER INFORMATION: Synthetic Oligonucleotide Sequence

<400> SEQUENCE: 44
gcccaacaag gcgatgatca ggagacacgg cccagactcc tacg                 44

<210> SEQ ID NO 45
<211> LENGTH: 1530
<212> TYPE: DNA
<213> ORGANISM: Megasphaera elsdenii
<220> FEATURE:
<221> NAME/KEY: misc_feature
<222> LOCATION: (895)..(895)
<223> OTHER INFORMATION: n is a, c, g, or t
<300> PUBLICATION INFORMATION:
<308> DATABASE ACCESSION NUMBER: AY038996.1
<309> DATABASE ENTRY DATE: 2002-10-15
<313> RELEVANT RESIDUES IN SEQ ID NO: (1)..(1530)

<400> SEQUENCE: 45
agagtttgat cctggctcag gacgaacgct ggcggcgtgc ttaacacatg caagtcgaac    60
gagaagagat gagaagcttg cttcttatcg attcgagtgg caaacgggtg agtaacgcgt   120
aagcaacctg cccttcagat ggggacaaca gctggaaacg gctgctaata ccgaatacgt   180 tcttttttgtc gcatggcaga gagaagaaag ggaggctctt cggagctttc gctgaaggag   240
gggcttgcgt ctgattagct agttggaggg gtaacggccc accaaggcga cgatcagtag   300
ccggtctgag aggatgaacg gccacattgg gactgagaca cggcccagac tcctacggga   360
ggcagcagtg gggaatcttc cgcaatggac gaaagtctga cggagcaacg ccgcgtgaac   420
gatgacggcc ttcgggttgt aaagttctgt tatacgggac gaatggcgta cgacggtcaa   480
tacccgtcgt aagtgacggt accgtaagag aaagccacgg ctaactacgt gccagcagcc   540
gcggtaatac gtaggtggca agcgttgtcc ggaattattg ggcgtaaagg gcgcgcaggc   600
ggcgtcgtaa gtcggtctta aaagtgcggg gcttaacccc gtgagggac cgaaactgcg   660 atgctagagt atcggagagg aaagcggaat tcctagtgta gcggtgaaat gcgtagatat   720
taggaggaac accagtggcg aaagcggctt tctggacgac aactgacgct gaggcgcgaa   780
agccagggga gcaaacggga ttagataccc cggtagtcct ggcggtaaac gatggatact   840
aggtgtagga ggtatcgacc ccttctgtgc cggagttaac gcaataagta tcccngcctg   900
gggagtacgg ccgcaaaggc tgaaactcaa aggaattgac ggggccccgc acaagcggtg   960
gagtatgtgg tttaattcga cgcacgcgaa gaaccttacc aagccttgac attgattgct  1020
atgggtagag atacccagtt cctcttcgga ggacaagaaa acaggtggtg cacggctgtc  1080
gtcagctcgt gtcgtgagat gttgggttaa gtcccgcaac gagcgcaacc cctatcttct  1140
gttaccagcg agttaagtcg gggactcagg agagactgcc gcagacaatg cggaggaagg  1200
cggggatgac gtcaagtcat catgcccctt atggcttggg ctacacacgt actacaatgg  1260

```
ctcttaatag agggaagcga aggagcgatc cggagcaaac cccaaaaaca gagtcccagt      1320
tcggattgca ggctgcaact cgcctgcatg aagcaggaat cgctagtaat cgcaggtcag      1380
catactgcgg tgaatacgtt cccgggcctt gtacacaccg cccgtcacac cacgaaagtc      1440
attcacaccc gaagccggtg aggtaacctt ttggagccag ccgtcgaagg tgggggcgat      1500
gattggggtg aagtcgtaac aaggtaaccg                                       1530
```